(12) United States Patent
Lee et al.

(10) Patent No.: US 9,080,049 B2
(45) Date of Patent: Jul. 14, 2015

(54) PH-SENSITIVE GRAFT COPOLYMER, MANUFACTURING METHOD FOR SAME, AND POLYMER MICELLES USING METHOD

(75) Inventors: Doo Sung Lee, Suwon-si (KR); Min Sang Kim, Suwon-si (KR); Bong Sup Kim, Suwon-si (KR)

(73) Assignee: RESEARCH & BUSINESS FOUNDATION SUNGKYUNKWAN UNIVERSITY, Suwon-Si, Gyeonggi-Do (KR)

(*) Notice: Subject to any disclaimer, the term of this patent is extended or adjusted under 35 U.S.C. 154(b) by 887 days.

(21) Appl. No.: 13/263,452

(22) PCT Filed: Apr. 9, 2010

(86) PCT No.: PCT/KR2010/002223
§ 371 (c)(1),
(2), (4) Date: Oct. 7, 2011

(87) PCT Pub. No.: WO2010/117248
PCT Pub. Date: Oct. 14, 2010

(65) Prior Publication Data
US 2012/0027690 A1 Feb. 2, 2012

(30) Foreign Application Priority Data

Apr. 9, 2009 (KR) .................. 10-2009-0031022

(51) Int. Cl.
| | |
|---|---|
| *A61K 8/72* | (2006.01) |
| *C08L 71/02* | (2006.01) |
| *A61K 9/107* | (2006.01) |
| *A61K 47/34* | (2006.01) |
| *A61K 49/00* | (2006.01) |
| *C08G 63/91* | (2006.01) |
| *C08G 81/00* | (2006.01) |
| *C08L 77/00* | (2006.01) |
| *A61K 9/127* | (2006.01) |
| *A61K 47/48* | (2006.01) |
| *C08L 87/00* | (2006.01) |

(52) U.S. Cl.
CPC .............. *C08L 71/02* (2013.01); *A61K 9/1075* (2013.01); *A61K 47/34* (2013.01); *A61K 47/482* (2013.01); *A61K 47/48192* (2013.01); *A61K 47/48215* (2013.01); *A61K 49/0021* (2013.01); *A61K 49/0054* (2013.01); *C08G 63/916* (2013.01); *C08G 81/00* (2013.01); *A61K 9/1273* (2013.01); *A61K 47/48815* (2013.01); *C08L 77/00* (2013.01); *C08L 87/00* (2013.01); *C08L 2205/05* (2013.01); *C08L 2666/24* (2013.01)

(58) Field of Classification Search
None
See application file for complete search history.

(56) References Cited

FOREIGN PATENT DOCUMENTS

| KR | 10-2007-0042944 A | 4/2007 |
|---|---|---|
| KR | 10-2008-0095130 A | 10/2008 |

OTHER PUBLICATIONS

International search report dated Jan. 26, 2011 of PCT/KR2010/002223 which is the parent application—6 pages.
Damom Sutton et al. 2007, Functionalized Micellar Systems for Cancer Targeted Drug Delivery.
Jordan J. Green et al. Jun. 2008, A Combinatorial Polymer Library Approach Yields Insight into Nonviral Gene Delivery.

*Primary Examiner* — James Rogers
(74) *Attorney, Agent, or Firm* — Knobbe, Martens, Olson & Bear, LLP

(57) ABSTRACT

The present document relates to a manufacturing method for pH-sensitive graft polymer micelles and a polymer micelle-type pharmaceutical composition containing the graft copolymer. The pH-sensitive graft copolymer micelles are usable as various markers and contrast agents for various molecular images for the diagnosis and treatment of diseases and a carrier for delivery of various medicines according to disease. The pH-sensitive graft copolymer forms micelles that can be used in target-oriented diagnosis and medicine release according to changes in the pH of a body. The polymer micelles are provided by inducing a graft copolymer of poly (β-amino ester) compounds which has a solubility in water depending on pH but is incapable of forming the micelles due to a self-assembly phenomenon, and hydrophilic poly(ethylene glycol) compounds.

6 Claims, 5 Drawing Sheets

PH-SENSITIVE GRAFT COPOLYMER, MANUFACTURING METHOD FOR SAME, AND POLYMER MICELLES USING METHOD

GOVERNMENT RIGHTS

The invention disclosed in this application was made with the support of the Korean government under Contract No. 2010-0027955 funded by Ministry of Science, ICT, and Future Planning and Basic Science Research Program through the National Research Foundation of Korea(NRF) funded by the Ministry of Education(2013R1A1A2063367). The Korean government has certain rights in the invention.

TECHNICAL FIELD

The present invention relates to the formation of pH-sensitive graft polymer micelles which are usable as a carrier for delivering a variety of therapeutic agents specific to certain disease as well as a variety of markers and contrast agents for molecular imaging to diagnose and treat disease, and to a polymer micelle-type pharmaceutical composition containing the graft copolymer. More specifically, the present invention relates to a pH-sensitive graft copolymer which forms micelles capable of carrying out target-oriented diagnosis and medicine release depending on changes in pH in vivo, by forming a graft copolymer of a poly(β-amino ester) compound which has solubility in water under pH conditions but is incapable of forming the micelles due to a self-assembly phenomenon, and a hydrophilic poly(ethylene glycol) based compound, and to a method of manufacturing the same.

BACKGROUND ART

Micelles are typically referred to as a spherical structure which is thermodynamically stable and of uniform form by low-molecular-weight materials having amphiphilic groups, that is, both hydrophilic and hydrophobic groups at the same time. In the case where a solution of the water-insoluble medicine in a compound having the micelle structure is introduced, the medicine is located inside the micelles, and such micelles are capable of carrying out the release of a target-oriented medicine in response to changes in temperature or pH in vivo and are thus regarded as having very high applicability as carriers for the delivery of medicines.

Korean Patent Application No. 10-2001-0035265 discloses the formation of micelles using poly(ethylene glycol) and a biodegradable polymer. These materials which are biodegradable are advantageous because they have biocompatibility, but are not sensitive to changes in vivo, for example, changes in pH, making it difficult to deliver the medicine to the desired sites.

Meanwhile, the pH condition in vivo typically falls in the pH range of 7.4~7.2, whereas the condition around abnormal cells such as cancer cells is known to be weak or strongly acidic in the pH range of 3.0~7.0. Recently, in order to deliver medicines specific to cancer cells, research into releasing medicines at a pH of 7.0 or less is ongoing.

U.S. Pat. No. 5,955,509 entitled "pH dependent polymer micelles" discloses a method of manufacturing pH-sensitive polymer micelles in which a block copolymer of poly(vinyl N-heterocycle) and poly(alkylene oxide) forms micelles at a pH of 6.0 or above and the micelles break down at a pH of 2~6, and Japanese Patent Publication No. 2002-179556, entitled "block copolymer-anticancer agent combined drug formulation" discloses a block copolymer of a hydrophilic poly(ethylene glycol) based compound and a hydrophobic polyamino acid based compound, which forms micelles at a specific pH.

DISCLOSURE

Technical Problem

Accordingly, an object of the present invention is to provide a graft copolymer formed by copolymerizing a poly(ethylene glycol) based compound with poly(β-amino ester), a method of manufacturing the same, and a polymer micelle-type diagnostic and therapeutic composition including the graft copolymer.

Technical Solution

In order to accomplish the above object, an aspect of the present invention provides a pH-sensitive graft copolymer, formed by copolymerizing (i) a poly(β-amino ester) compound (A); (ii) a poly(ethylene glycol) based compound (B); and (iii) one or more compounds selected from the group consisting of bile acid, a cholesterol based compound, and a cancer-targeting factor.

In this aspect, the poly(β-amino ester) in the graft copolymer may include a tertiary amine group which is ionized at a pH of less than 7.0.

In this aspect, the graft copolymer may form a micelle at a pH of 7.0~7.4 (particularly 7.2~7.4), and the micelle may break down at a pH ranging from 6.5 to less than 7.0.

In this aspect, the graft copolymer may be a compound represented by the chemical formula below:

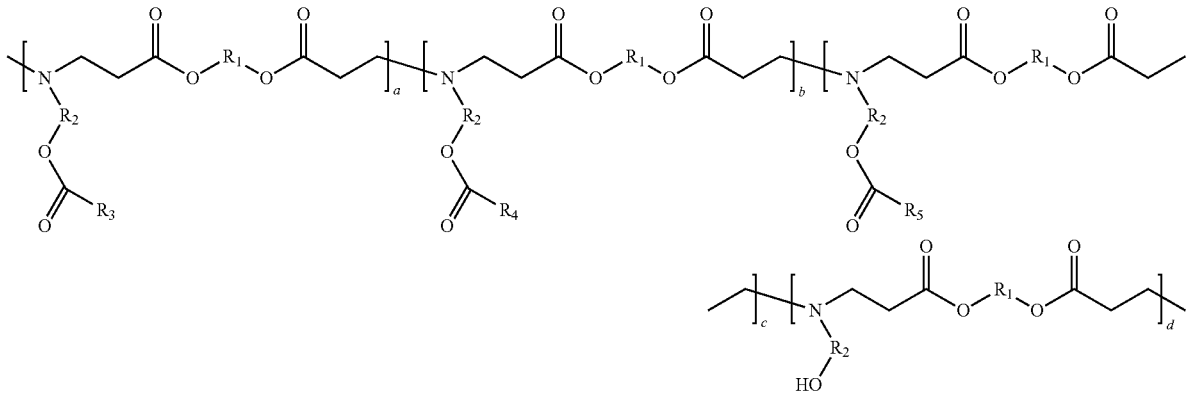

wherein $R_1=(CH)_m$
$R_2=(CH)_n$
$R_3$=a poly(ethylene glycol) based compound
$R_4$, $R_5$=a bile acid or cholesterol based compound, or a cancer-targeting factor In this aspect, the bile acid based compound or the cholesterol based compound may be one or more selected from the group consisting of cholic acid, chenodeoxycholic acid, glycocholic acid, taurocholic acid, deoxycholic acid, lithocholic acid, and cholesterol chloroformate.

In this aspect, the poly(ethylene glycol) based compound (B) and the poly(β-amino ester) compound (A) may be respectively contained in amounts of 1~30 wt % and 99~70 wt % in the graft copolymer.

In this aspect, the poly(ethylene glycol) based compound may have a terminal which is substituted with a functional group selected from the group consisting of a carboxyl group, an amine group, and a hydroxyl group.

In this aspect, the poly(ethylene glycol) based compound may have a molecular weight ranging from 500 to 5000.

In this aspect, the poly(β-amino ester) compound may be formed by polymerizing (a) a bisacrylate compound; and (b) an amine based compound.

As such, the bisacrylate compound may be one or more selected from the group consisting of ethylene glycol diacrylate, 1,4-butanediol diacrylate, 1,3-butanediol diacrylate, 1,6-hexanediol diacrylate, 1,6-hexanediol ethoxylate diacrylate, 1,6-hexanediol propoxylate diacrylate, 3-hydroxy-2,2-dimethylpropyl-3-hydroxy-2,2-dimethylpropionate diacrylate, 1,7-heptanediol diacrylate, 1,8-octanediol diacrylate, 1,9-nonanediol diacrylate, 1,10-decanediol diacrylate, neopentylglycol diacrylate, pentaerythritol diacrylate, and trimethylolpropane benzoate.

Furthermore, the amine based compound may be one or more selected from the group consisting of ethanol amine, 3-amino-1-propanol, 2-amino-1-propanol, 1-amino-2-propanol, 3-amino-1,2-propanediol, 2-amino-1,3-propanediol, serinol, 2-(2-aminoethoxy)ethanol, 2-amino-2-methyl-1,3-propanediol, L-threninol, 2-amino-1-butanol, 2-amino-2-methyl-1-propanol, 4-amino-1-propanol, 4-amino-2-butanol, 2-amino-1-pentanol, 2-amino-3-methyl-1-butanol, 2-amino-1-pentanol, 4-amino-1-butanol, 5-amino-1-pentanol, valinol, 6-amino-1-hexanol, 7-amino-1-heptanol, 8-amino-1-octanol, 10-amino-1-decanol, 2-amino-2-ethyl-1,3-propanediol, and N,N-bis(2-hydroxyethyl)ethylene diamine.

Furthermore, the molar ratio of the bisacrylate compound to the amine based compound may be 1:0.5~1.6.

In this aspect, the molar ratio of the poly(ethylene glycol) based compound to the poly(β-amino ester) compound may be 1:1~1:10.

Another aspect of the present invention provides a polymer micelle-type pharmaceutical composition, comprising (a) the above-mentioned graft copolymer; and (b) a marker or a contrast agent for molecular imaging used to diagnose disease or a therapeutic agent for treating disease, which is able to be chemically bound to the graft copolymer.

In this aspect, the polymer micelle may have a diameter of 10~200 nm.

In this aspect, the marker for molecular imaging used to diagnose disease, which is able to be chemically bound to the graft copolymer, may be one or more selected from the group consisting of pyrene, RITC (rhodamine B isothiocyanate), FITC (fluorescein isothiocyanate), phycoerythrin (PE), ICG (indocyanine green), PSA (prostate-specific antibody), AFP (alpha-fetoprotein), HCG (human chorionic gonadotropin), CA 125 (cancer antigen 125), CA 15-3 (cancer antigen 15-3), and CEA (carcinoembryonic antigen).

In this aspect, the contrast agent for molecular imaging used to diagnose disease, which is able to be chemically bound to the graft copolymer, may be one or more selected from the group consisting of a variety of paramagnetic materials, including iron oxide, manganese oxide, zinc oxide, and gadolinium oxide.

In this aspect, the therapeutic agent for treating disease, which is able to be chemically bound to the graft copolymer, may be one or more selected from the group consisting of an anticancer agent including paclitaxel (PTX), doxorubicin (DOX), docetaxel (DOCE) and so on, an antibacterial agent, steroids, an anti-inflammatory painkiller, a sexual hormone, an immunosuppressive agent, an antiviral agent, an anesthetic, an antinauseant, an antihistamine agent, and a protein including bovine serum albumin, human serum albumin, and human growth hormone.

A further aspect of the present invention provides a method of manufacturing a pH-sensitive graft copolymer as shown in the scheme below.

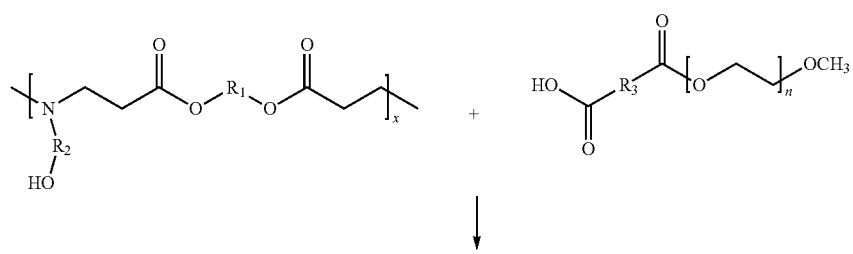

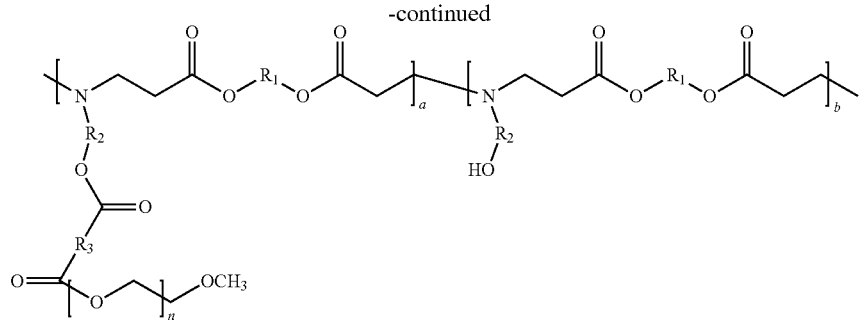

wherein $R_1$, $R_2$, $R_3$, and $R_4$ are a C1-12 alkyl group; and a, b, x and n are a natural number ranging from 1 to 200.

In this aspect, the graft copolymer may be a compound manufactured by the scheme below.

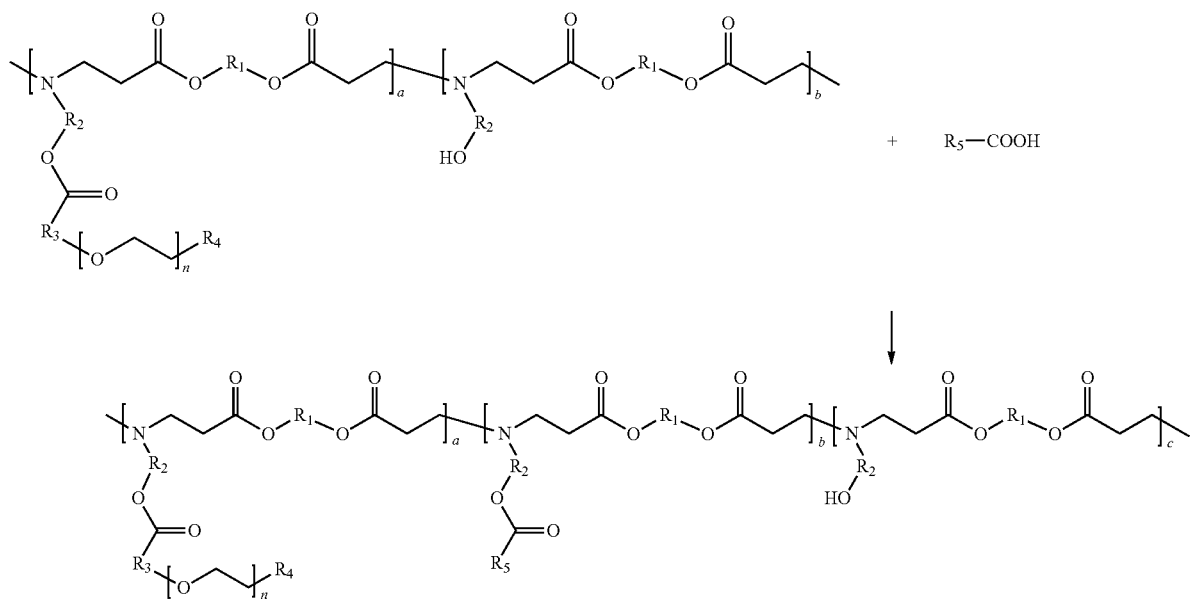

wherein $R_1$, $R_2$, $R_3$, and $R_4$ are a hydrogen atom or a C1~12 alkyl group; a, b, c and n are a natural number ranging from 1 to 200; and $R_5$ is a bile acid based compound, a cholesterol based compound or a cancer-targeting factor.

In this aspect, the graft copolymer may be a compound manufactured by the scheme below.

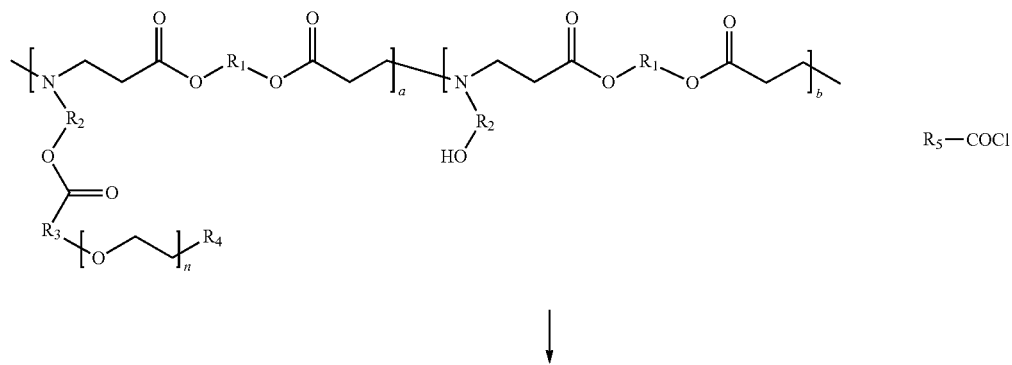

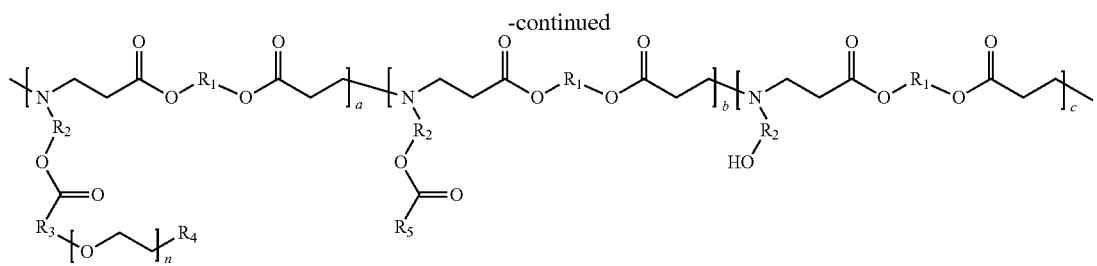

wherein $R_1$, $R_2$, $R_3$, and $R_4$ are a hydrogen atom or a C1~12 alkyl group; a, b, c and n are a natural number ranging from 1 to 200; and $R_5$ is a cholesterol based compound.

In this aspect, the pH-sensitive graft copolymer may be manufactured as shown in the scheme below.

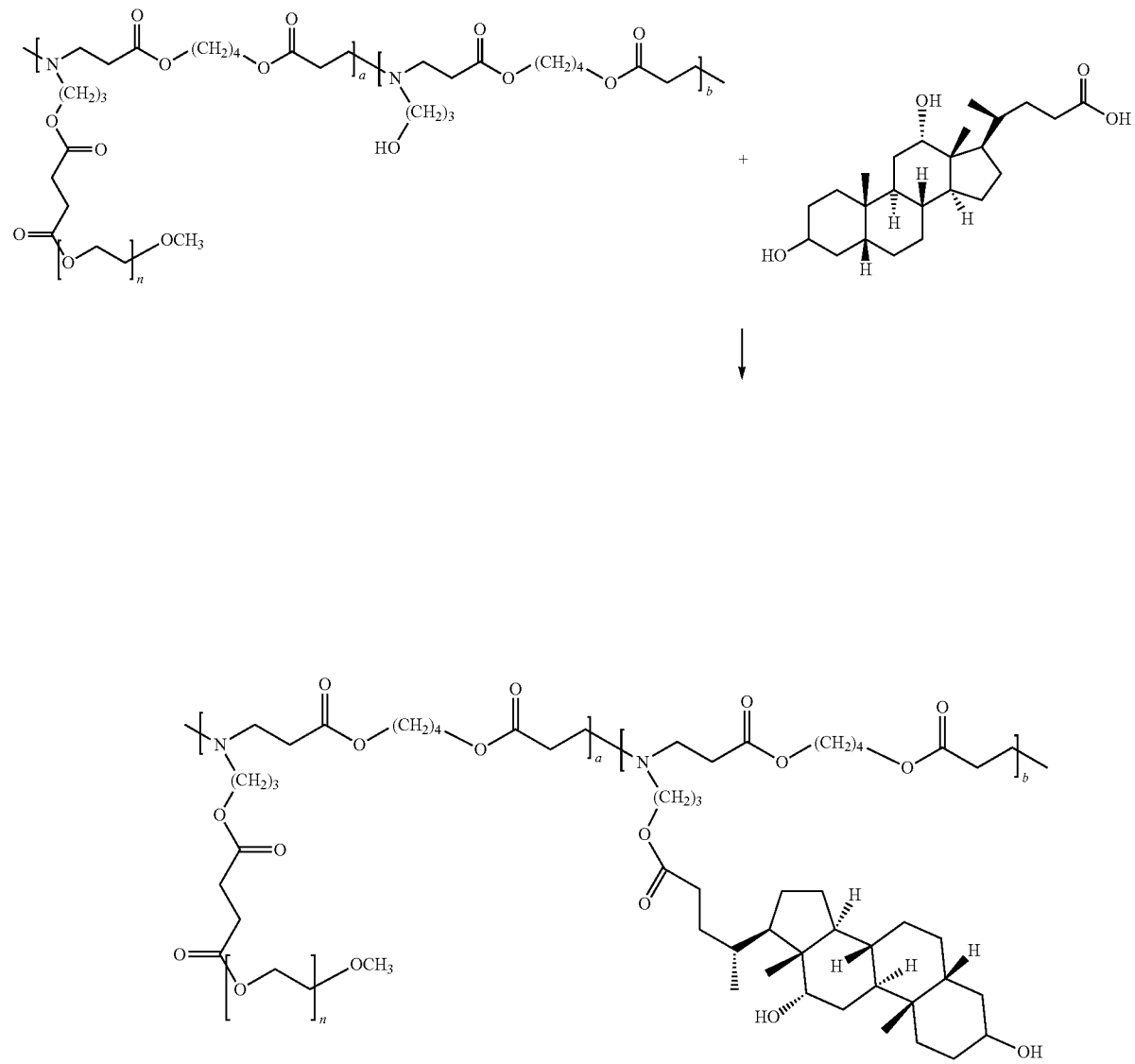

wherein a, b, and n are a natural number ranging from 1 to 200.

In this aspect, the pH-sensitive graft 5 copolymer may be manufactured as shown in the scheme below.

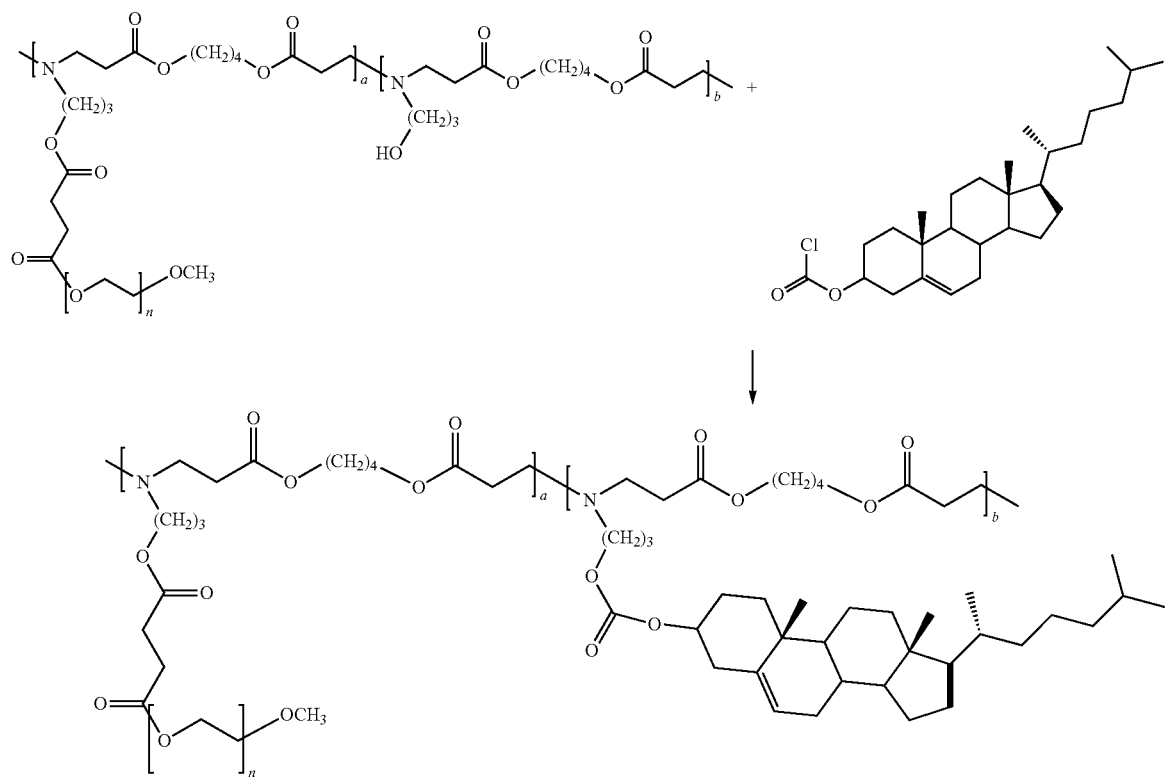
wherein a, b, and n are a natural number ranging from 1 to 200.
In this aspect, the pH-sensitive graft copolymer may be manufactured as shown in the scheme below.

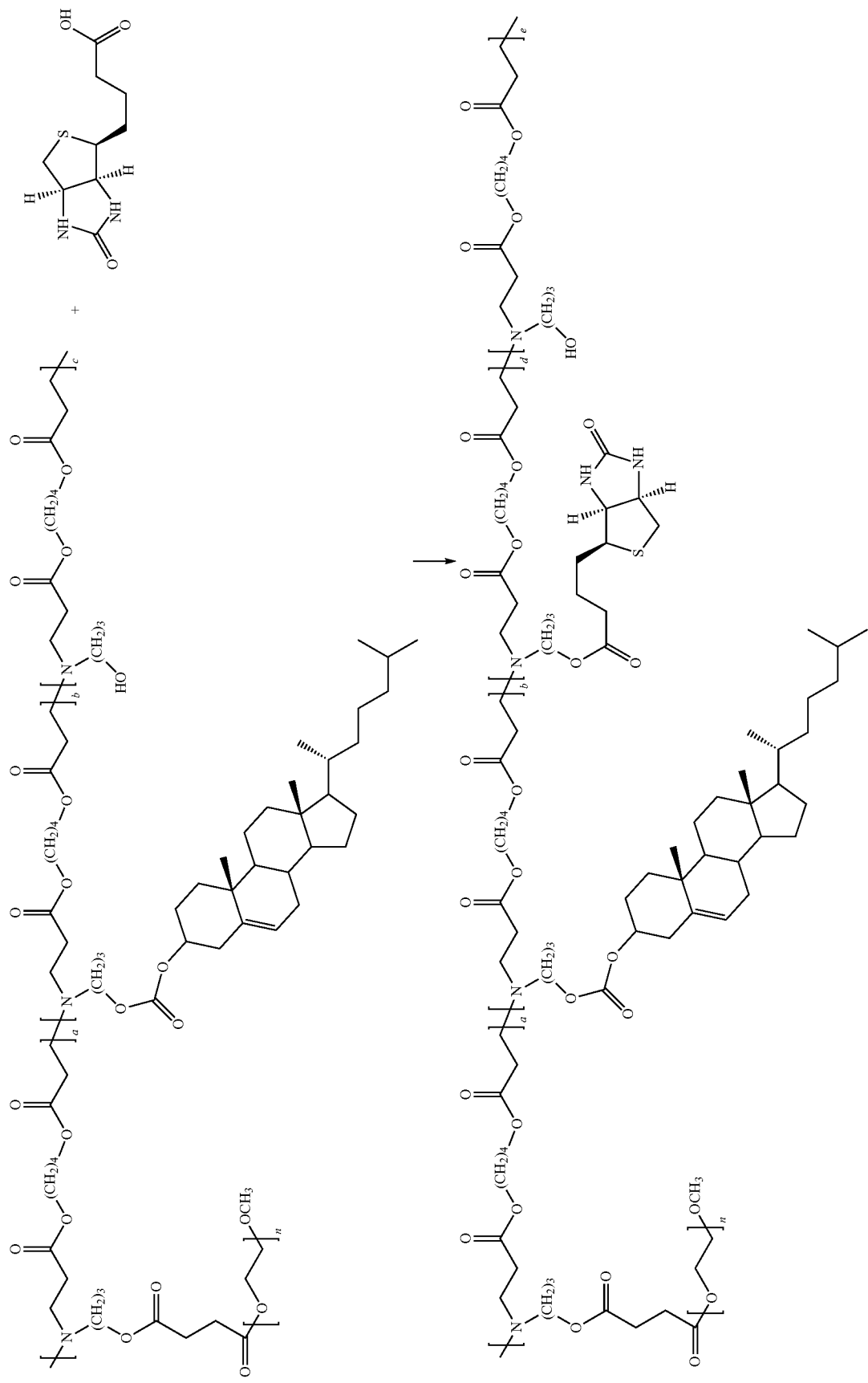

wherein a, b, c, d, e and n are a natural number ranging from 1 to 200.

Advantageous Effects

According to the present invention, a graft copolymer is formed by copolymerizing a poly(β-amino ester) compound which has solubility in water depending on the pH but is incapable of forming micelles due to a self-assembly phenomenon with a hydrophilic poly(ethylene glycol) based compound, thereby retaining pH sensitivity, and as well, the graft copolymer has a hydroxyl group on the side chain thereof and thus can be chemically bound with a marker and a contrast agent for molecular imaging used to diagnose disease and a therapeutic agent for treating disease, and thereby can be used for target-oriented medicine delivery and diagnosis depending on changes in pH in vivo.

BEST MODE

Figure 1:
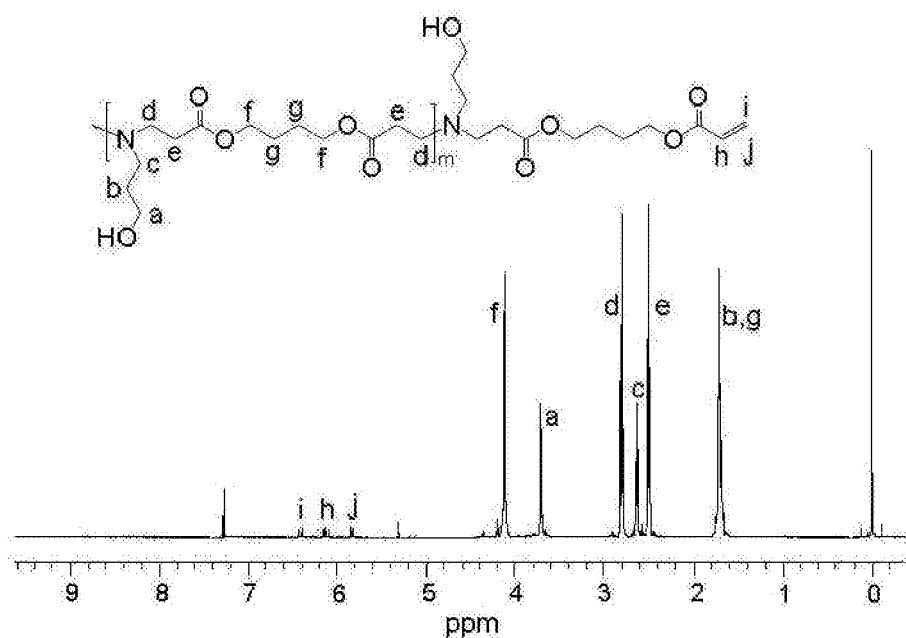
FIG. 1 is a $^1$H-NMR graph of poly(β-amino ester) showing the results of synthesizing poly(β-amino ester) resulting from a Michael reaction of a poly(β-amino ester) precursor, namely, 3-amino 1-propanol and 1,4-butanediol diacrylate.
Figure 2:
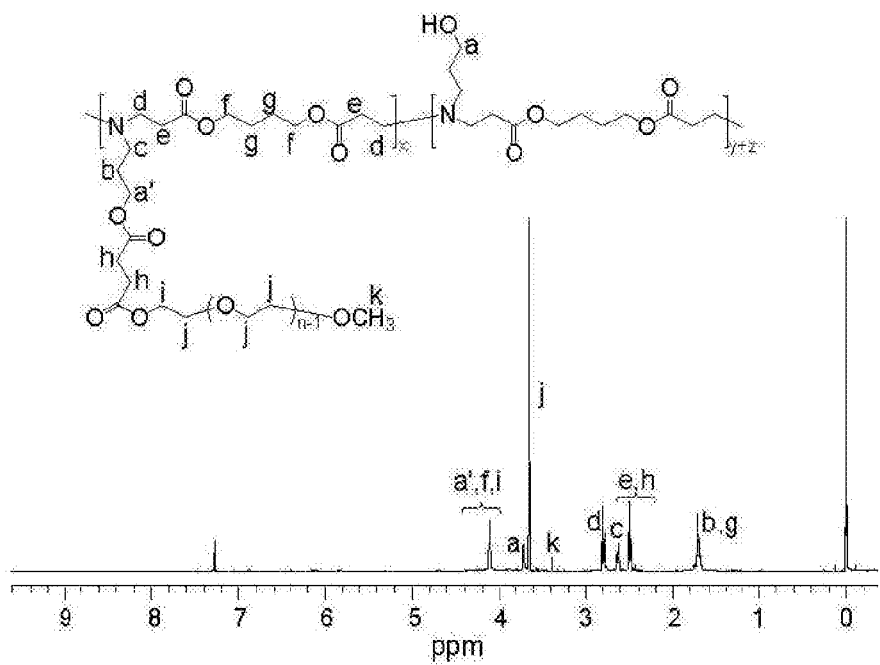
FIG. 2 is a $^1$H-NMR graph of a graft copolymer resulting from the reaction between the synthesized poly(β-amino ester) and poly(ethylene glycol)

Hereinafter, embodiments of the present invention will be described in detail while referring to the accompanying drawings. Throughout the drawings, it is noted that the same reference numerals are used to refer to the same components or parts. Furthermore, in the description of the present invention, known techniques, even if they are pertinent to the present invention, may be omitted if they would make the characteristics of the invention unclear.

As used herein, when acceptable errors or the numerical values are disclosed in the description, the terms "about", "substantially", etc., are used to mean ones close to the acceptable errors or the numerical values, and these terms are used to intend to prevent the disclosure including the exact or absolute numerical values proposed for the better understanding of the present invention from being unduly used by unconscientious infringers.

The present invention provides a pH-sensitive graft copolymer formed by copolymerizing (i) a poly(β-amino ester) compound (A), (ii) a poly(ethylene glycol) based compound (B), and (iii) one or more compounds selected from the group consisting of bile acid, a cholesterol based compound, and a cancer-targeting factor, and a method of manufacturing the same.

In addition, the present invention provides a polymer micelle-type pharmaceutical composition, comprising a pH-sensitive graft copolymer and a variety of diagnostic agents and therapeutic agents able to be chemically bound to the graft copolymer.

Below is a detailed description of the present invention.

According to the present invention, a poly(β-amino ester) compound that is sensitive to pH, a poly(ethylene glycol) based compound that is hydrophilic, and one or more compounds selected from the group consisting of bile acid, a cholesterol based compound, and a cancer-targeting factor are graft copolymerized, thereby obtaining a graft copolymer which is sensitive to changes in pH in vivo and is able to form micelles in a specific pH range and to form a chemical bond with a marker and a contrast agent for molecular imaging used to diagnose disease and a therapeutic agent for treating disease because of a hydroxyl group provided on the side chain thereof. The present inventors discovered that the use of poly(β-amino ester) alone may exhibit pH dependency but is incapable of forming micelles due to a self-assembly phenomenon, and thus the poly(β-amino ester) is graft copolymerized with a hydrophilic poly(ethylene glycol) based compound to thus form a graft copolymer so that a marker and a contrast agent for molecular imaging used to diagnose disease and a variety of therapeutic agents may be chemically bound to the polymer micelles, instead of forming a graft copolymer according to conventional techniques, whereby the resulting graft copolymer may form a micelle structure that enables targeted release at a specific pH and thus may be applied as a carrier for the release of a target-oriented medicine to diagnose and treat disease.

The pH-sensitive micelles according to the present invention may be stably formed at a specific pH, for example pH 7.0~7.4, preferably 7.2~7.4, corresponding to the pH range of normal cells in vivo, and may break down at a pH of less than 7.0 corresponding to the pH range of abnormal cells such as cancer cells, so that the pH-sensitive micelles may be used as a carrier for the release of a target-oriented medicine that is a therapeutic agent that treats the corresponding disease while diagnosing cancer cells in a targeted manner by means of the release of a diagnostic agent chemically bound to the micelles. Specifically, at low pH (a pH of less than 7.0), because the degree of ionization of tertiary amine present in poly(β-amino ester) may increase, the entire PAE is rendered water-soluble, making it impossible to form micelles, and at a pH of 7.0 or above, the degree of ionization of PAE may decrease, thus manifesting hydrophobic properties, thereby forming micelles based on self assembly.

Also, the graft copolymer able to form the pH-sensitive micelles may transfer material, which may deliver genes and medicines and may also diagnose and treat disease, to abnormal cells, and thereby may be applied to end uses that carry out diagnosis and treatment at the same time.

Also in the present invention, cancer-targeting micelles in which the micelles are formed in the pH range of 7.0~7.4 corresponding to the normal conditions in vivo and break down at a pH of less than 7.0 under abnormal conditions such as that of cancer cells were designed and applied, but the components of the graft copolymer, the molar ratio thereof, the molecular weight and/or the side-chain functional group may be appropriately varied, so that target-oriented micelles may be designed and applied to the field of gene variation or other applications, in addition to cancer cells.

As one component of the graft copolymer that forms the pH-sensitive micelles according to the present invention, a biodegradable compound which is typically known to be hydrophilic in the art, for example, a poly(ethylene glycol) based compound may be used. Particularly useful is a poly(ethylene glycol) based compound the terminal of which has a monofunctional group such as a carboxyl group or the like so as to react with poly(β-amino ester) that is a pH-sensitive polymer, and there is exemplified a compound represented by Chemical Formula 1 wherein the terminal of the molecule is substituted with a carboxyl group.

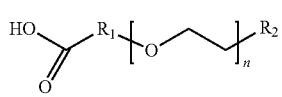

[Chemical Formula 1]

wherein $R_1$ and $R_2$ are a hydrogen atom or a C1~12 alkyl group, and n is a natural number ranging from 1 to 200.

The alkyl group indicates a linear or branched lower saturated aliphatic hydrocarbon, for example, methyl, ethyl, n-propyl, isopropyl, n-butyl, s-butyl, isobutyl, t-butyl and n-pentyl.

The number average molecular weight (Mn) of the poly(ethylene glycol) based compound is not particularly limited, but preferably falls in the range of 500~5000. If the poly(ethylene glycol) based compound has a number average molecular weight (Mn) less than 500 or exceeding 5000, it is difficult to adjust the molecular weight of a final graft copolymer and it is not easy to form micelles using the graft copolymer.

Another component of the graft copolymer that forms the pH-sensitive micelles according to the present invention is a poly(β-amino ester) compound that is hydrophobic and is pH-sensitive at the same time.

The poly(β-amino ester) compound has ionization properties in which solubility in water may vary depending on the pH due to a tertiary amine group present therein, and thereby the micelle structure may form and/or may break down depending on changes in pH in vivo as mentioned above. The poly(β-amino ester) compound may be prepared using a method typically known in the art, and for example may be synthesized by polymerizing a bisacrylate compound with an amine based compound.

As such, bisacrylate may be represented by Chemical Formula 2 below, and examples thereof may include but are not limited to ethylene glycol diacrylate, 1,4-butanediol diacrylate, 1,3-butanediol diacrylate, 1,6-hexanediol diacrylate, 1,6-hexanediol ethoxylate diacrylate, 1,6-hexanediol propoxylate diacrylate, 3-hydroxy-2,2-dimethylpropyl3-hydroxy-2,2-dimethylpropionate diacrylate, 1,7-heptanediol diacrylate, 1,8-octanediol diacrylate, 1,9-nonanediol diacrylate, 1,10-decanediol diacrylate, neopentyl glycol diacrylate, pentaerythritol diacrylate, trimethylolpropane benzoate or mixtures thereof.

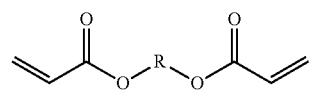

[Chemical Formula 2]

wherein R is a C1~30 alkyl group.

Also, the amine based compound may be represented by Chemical Formula 3 below.

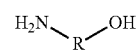

[Chemical Formula 3]

wherein n is a C1~20 alkyl group.

Examples of the amine based compound include but are not limited to ethanol amine, 3-amino-1-propanol, 2-amino-1-propanol, 1-amino-2-propanol, 3-amino-1,2-propanediol, 2-amino-1,3-propanediol, serinol, 2-(2-aminoethoxy)ethanol, 2-amino-2-methyl-1,3-propanediol, L-threninol, 2-amino-1-butanol, 2-amino-2-methyl-1-propanol, 4-amino-1-propanol, 4-amino-2-butanol, 2-amino-1-pentanol, 2-amino-3-methyl-1-butanol, 2-amino-1-pentanol, 4-amino-1-butanol, 5-amino-1-pentanol, valinol, 6-amino-1-hexanol, 7-amino-1-heptanol, 8-amino-1-octanol, 10-amino-1-decanol, 2-amino-2-ethyl-1,3-propanediol, N,N-bis(2-hydroxyethyl)ethylene diamine, etc.

Upon preparation of poly(β-amino ester), the molar ratio of the bisacrylate compound to the amine based compound may be 1:0.5~1.6. If the molar proportion of the amine based compound is less than 0.5 or exceeds 1.6, the reaction is not efficient or a crosslinking reaction may take place, making it difficult to form a polymer.

According to the present invention, the poly(β-amino ester) and the pH-sensitive graft copolymer, respectively resulting from polymerization of poly(β-amino ester) as mentioned above and graft copolymerization of hydrophilic poly(ethylene glycol) based compound and hydrophobic poly(β-amino ester) may be represented by Chemical Formulas 4 and 5 below.

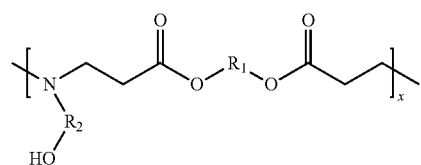

[Chemical Formula 4]

wherein $R_1$ and $R_2$ are a hydrogen atom or a C1~12 alkyl group, and x is a natural number ranging from 1 to 200.

[Chemical Formula 5]

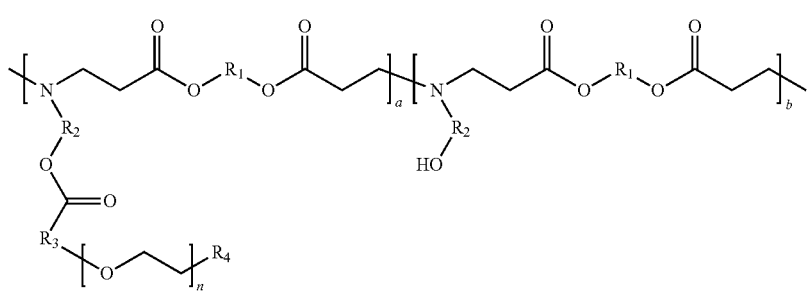

wherein R is a hydrogen atom or a C1~12 alkyl group, and a, b and n are a natural number ranging from 1 to 200.

The graft copolymer represented by Chemical Formula 5 may form micelles via self assembly or such micelles may break down depending on changes in pH because of amphiphilicity and the pH-sensitivity as mentioned above. When the pH is 7.0~7.4 and preferably 7.2~7.4, the micelles may form, and when the pH is in the range from 6.5 to less than 7.0, the micelles break down. In particular, the graft copolymer according to the present invention may exhibit superior sensitivity within a pH range of 0.2.

The molecular weight of the graft copolymer is not particularly limited, but falls in the range of 10,000~20,000. If the molecular weight thereof is less than 10,000, it is difficult for graft copolymer micelles to form at a specific pH, and even when they do form, such micelles may dissolve in water and may thus easily break down. In contrast, if the molecular weight thereof exceeds 20,000, the hydrophilic/hydrophobic balance may break, and the micelles do not form but may precipitate at a specific pH.

In the pH-sensitive graft copolymer according to the present invention, the poly(ethylene glycol) based compound (B) may be contained in an amount of 1~30 wt %, and preferably 5~10 wt %. If the amount of the poly(ethylene glycol) based compound is less than 1 wt %, the graft copolymer does not form micelles but may precipitate. In contrast, if the amount thereof exceeds 30 wt %, the micelles cannot be formed due to crosslinkage. Furthermore, the graft copolymer may be provided in various graft forms by adjusting the molar ratio of the poly(ethylene glycol) based compound and the poly(β-aminoester).

The pH-sensitive graft copolymer according to the present invention may be manufactured using a method typically known in the art, and for example may be synthesized as shown in Scheme 1 or 2 below.

[Scheme 1]

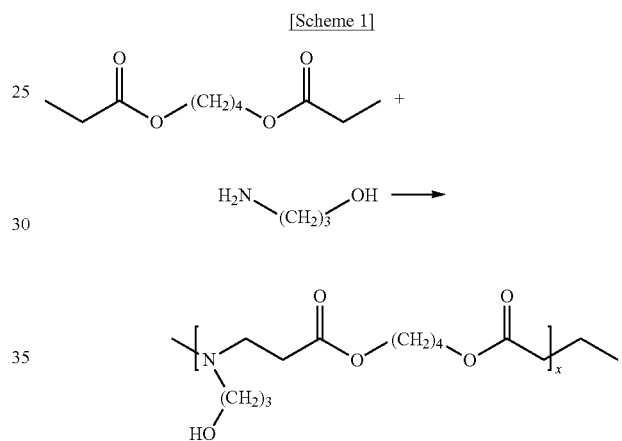

According to an embodiment of the manufacturing method as shown in Scheme 1, poly(β-amino ester) is formed from bisacrylate having an acrylate terminal group and 3-amino 1-propanol via an addition reaction, called a Michael reaction, typically known in the art, and the poly(β-amino ester) thus formed has a tertiary amine that is a pH-sensitive group and a hydroxyl group as a side chain. As shown in Scheme 2, this polymer is graft copolymerized with the poly(ethylene glycol) based compound having a carboxyl group substitution at the terminal thereof, thus obtaining the graft copolymer represented by Chemical Formula 5.

[Scheme 2]

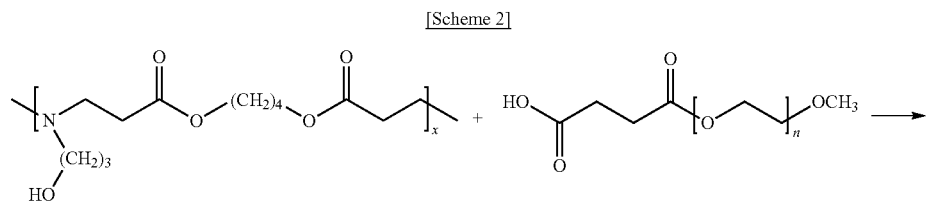

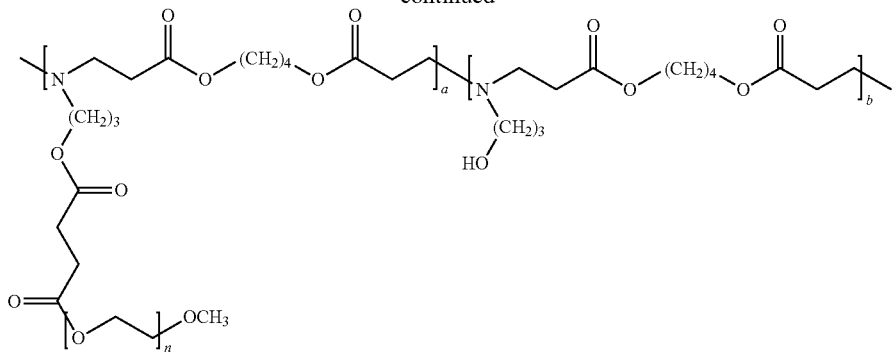

wherein $R_1$, $R_2$, $R_3$ and $R_4$ are a C1-12 alkyl group; and a, b, x and n are a natural number ranging from 1 to 200.

According to an embodiment of the manufacturing method as shown in Scheme 2, the poly(β-amino ester) formed according to Scheme 1, having a tertiary amine that is a pH-sensitive group and a hydroxyl group as a side chain, is graft copolymerized with the poly(ethylene glycol) based compound having a carboxyl group substitution at the terminal thereof to thus afford the graft copolymer represented by Chemical Formula 5. As such, in the manufacture of the graft copolymer, an organic solvent, such as dichloromethane, tetrahydrofuran, dimethyl sulfoxide, dimethyl formamide, etc., may be used.

The molar ratio of the poly(ethylene glycol) based compound to the poly(β-amino ester) compound may be 1:1~1:10.

Also as represented by Scheme 3 below, a graft copolymer grafted with a hydrophobic material may be obtained via the grafting of a bile acid based compound or a cholesterol based compound.

wherein $R_1$, $R_2$, $R_3$, $R_4$ are a hydrogen atom or a C1~12 alkyl group, and a, b, c and n are a natural number ranging from 1 to 200.

As such, $R_5$ is a bile acid based compound, a cholesterol based compound, or a cancer-targeting factor, and examples thereof include but are not limited to one or more selected from the group consisting of cholic acid, chenodeoxycholic acid, glycocholic acid, taurocholic acid, deoxycholic acid, lithocholic acid, cholesterol chloroformate, and a cancer-targeting factor including biotin and folic acid.

With respect to the PEA-PEG graft polymer, the bile acid based compound or the cholesterol based compound or the cancer-targeting factor may be formed at a molar ratio of 1:1~1:30, on the basis of a site wherein the above compound may be attached to the polymer.

Also, the graft copolymer according to the present invention may be provided in the form of a polymer including a cholesterol compound, as shown in Scheme 4 below.

[Scheme 3]

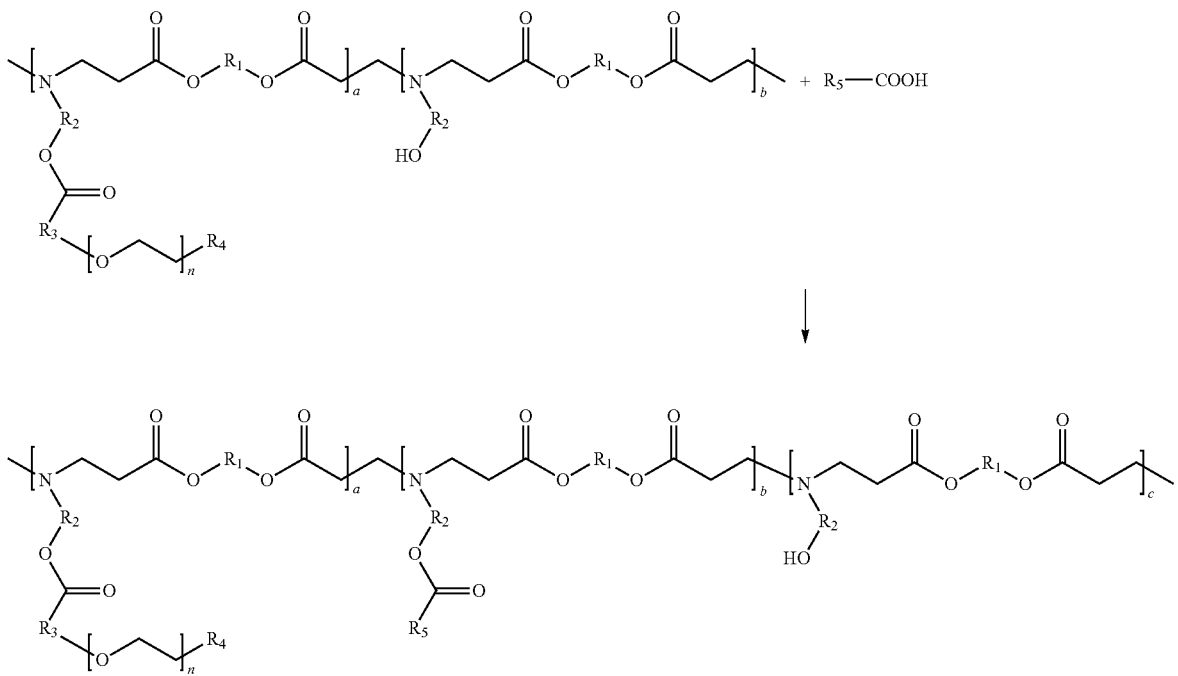

[Scheme 4]
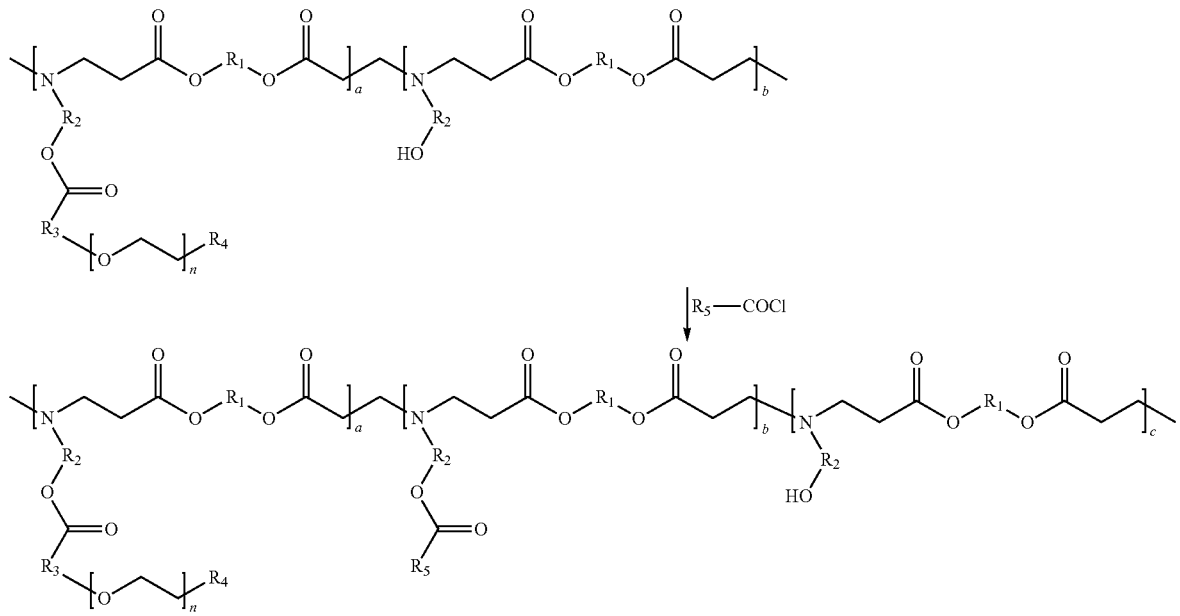
wherein $R_1$, $R_2$, $R_3$, $R_4$ are a hydrogen atom or a C1~12 alkyl group, and a, b, c and n are a natural number ranging from 1 to 200.
The resultant graft copolymer is obtained via a reaction with $R_5$ which is a cholesterol based compound, for example, a cholesterol derivative such as cholesterol chloroformate.
[Scheme 5]
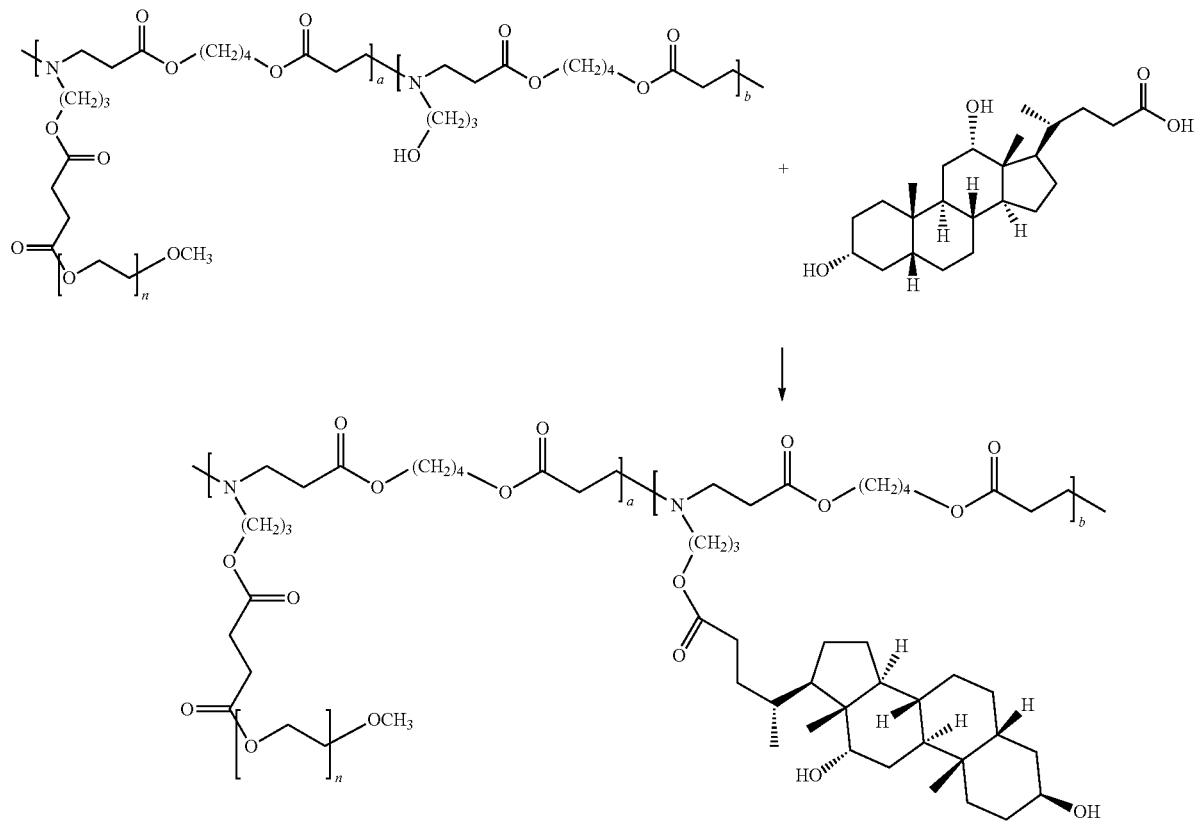

wherein a, b, and n are a natural number ranging from 1 to 200.

According to an embodiment of the manufacturing method as shown in Scheme 5, the poly(β-amino ester)-poly(ethylene glycol) graft copolymer resulting from Scheme 2 and a bile acid based compound such as deoxycholic acid are subjected to dehydration typical of the art, yielding a graft copolymer of poly(ethylene glycol) and deoxycholic acid.

As in the above graft copolymer, an embodiment of the manufacturing method of a copolymer grafted with a hydrophobic material is depicted in Scheme 6 below.

[Scheme 6]

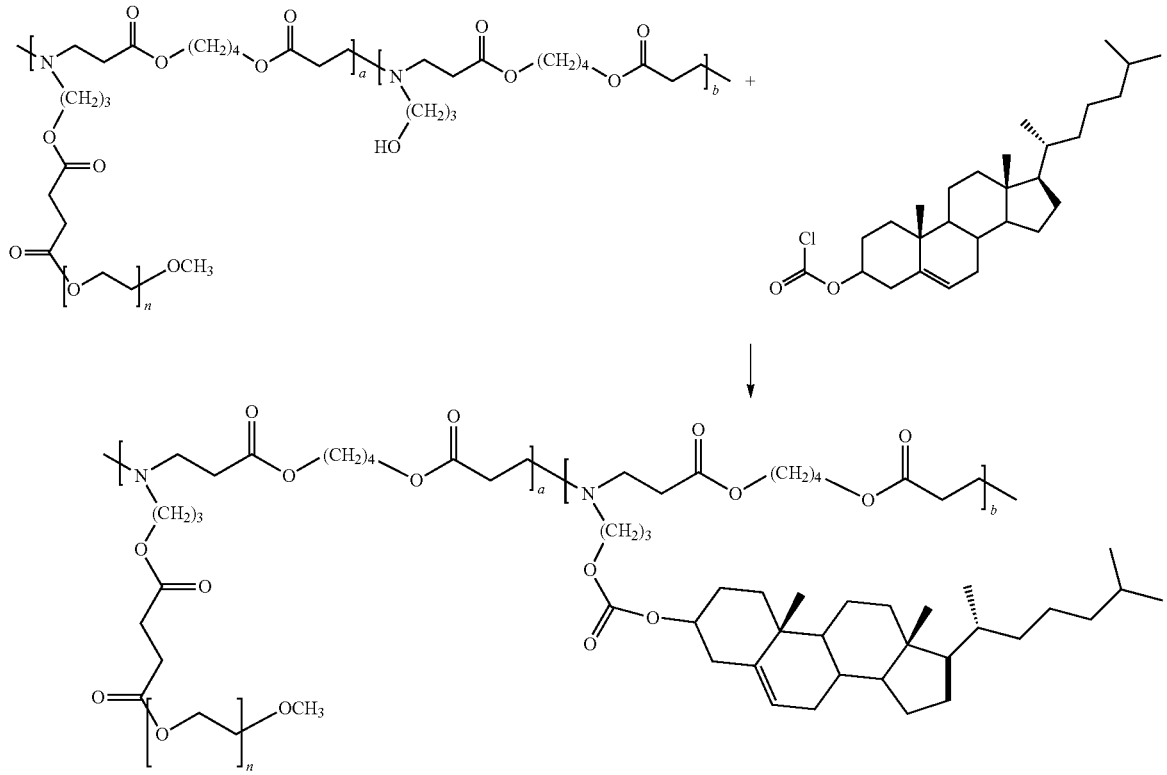

wherein a, b, and n are a natural number ranging from 1 to 200.

According to an embodiment for grafting of the cancer-targeting factor, biotin which is a kind of cancer-targeting factor may react with the graft copolymer obtained as shown in Scheme 2, yielding a graft copolymer as shown in Scheme 7 below.

[Scheme 7]

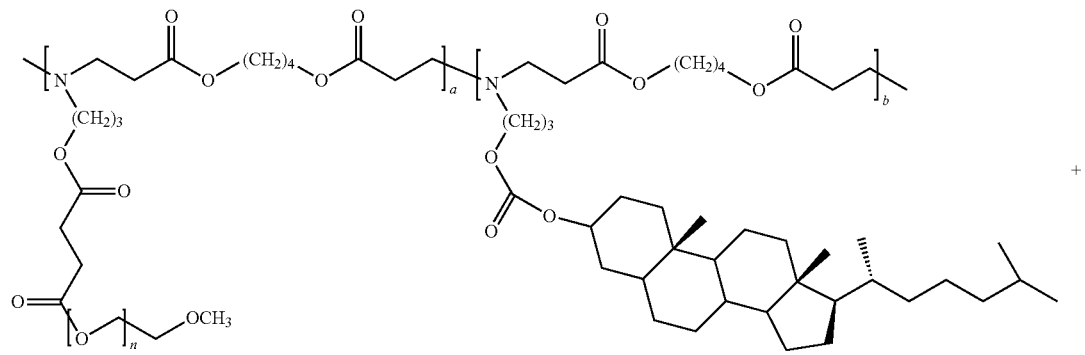

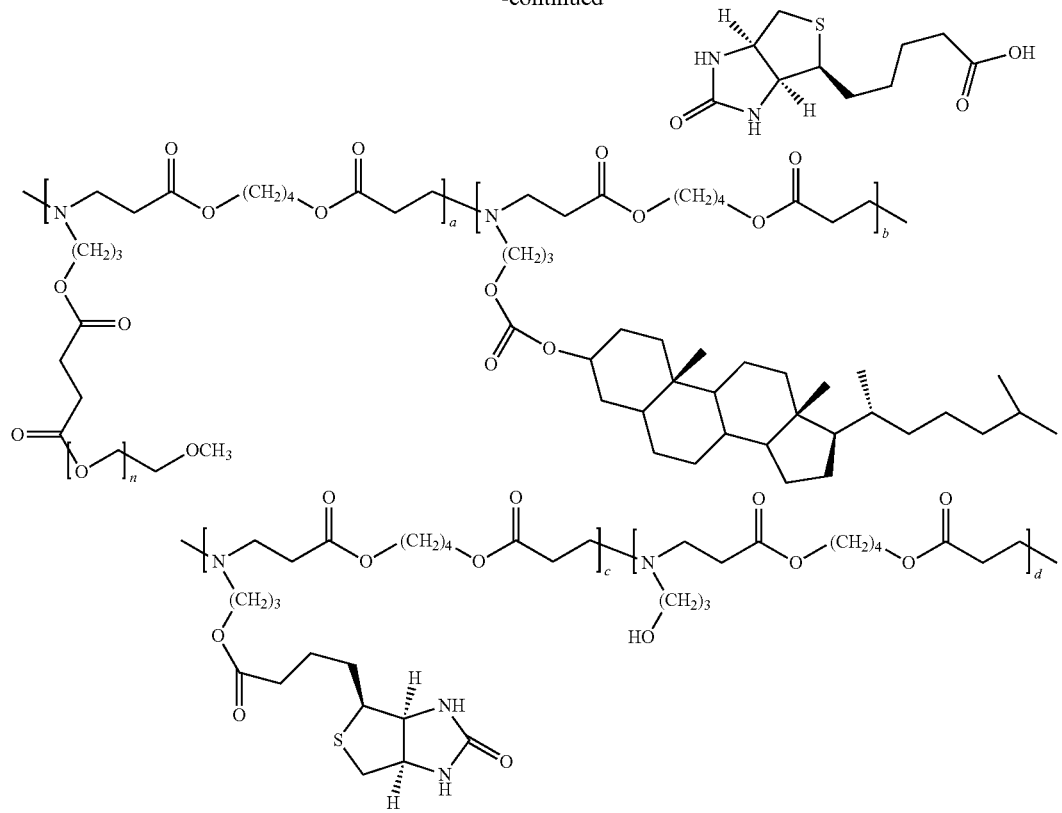

wherein a, b, c, d, e and n are a natural number ranging from 1 to 200.

According to the embodiment of the present invention, the graft copolymer may be represented by Chemical Formula 6 below.

[Chemical Formula 6]

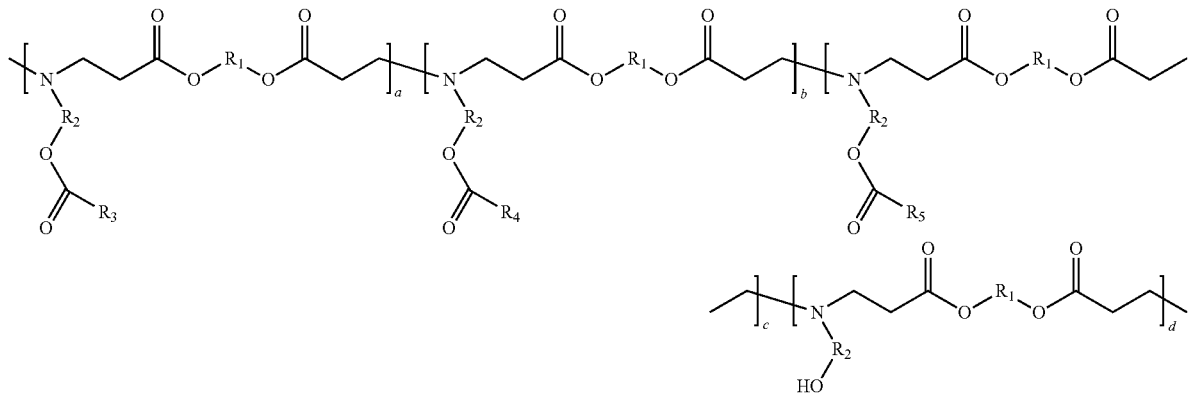

wherein $R_1=(CH)_m$
$R_2=(CH)_n$
$R_3$=a poly(ethylene glycol) based compound
$R_4$, $R_5$=a bile acid or cholesterol based compound, or a cancer-targeting factor In order to measure the molecular weight of the graft copolymer synthesized as mentioned above, GPC (Gel Permeation Chromatography) was adopted, and $^1$H-NMR was used to calculate the molar ratio of grafted hydrophilic material, hydrophobic material and cancer-targeting factor. Also to measure changes in the concentration and size of micelles in relation to changes in pH, a fluorescence spectrometer (FL) and DLS (Dynamic Light Scattering) were used, and the applicability as the pH-sensitive micelles could be confirmed by the actual results of analysis.

In addition, the present invention provides a polymer micelle-type pharmaceutical composition comprising (a) the above-mentioned graft copolymer which forms micelles depending on changes in pH; and (b) a marker or a contrast agent for molecular imaging used to diagnose disease or a therapeutic agent to treat disease, which is capable of being chemically bound to the graft copolymer.

The polymer micelle-type pharmaceutical composition may form micelles when injected in vivo, and then the micelles break down when reaching a topical position having low pH such as cancer cells, thus releasing the marker and contrast agent for molecular imaging used to diagnose disease and the therapeutic agent for treating disease, which are chemically bound to the graft copolymer, thereby achieving the delivery of a target-oriented medicine.

The diagnostic and therapeutic materials able to be chemically bound to the polymer micelle-type graft copolymer according to the present invention may be used without particular limitation, and examples thereof include but are not limited to a diagnostic agent, including pyrene, RITC, FITC (fluorescein isothiocyanate), phycoerythrin (PE), ICG (indocyanine green), PSA (prostate-specific antibody), AFP (alpha-fetoprotein), HCG (human chorionic gonadotropin), CA 125 (cancer antigen 125), CA 15-3 (cancer antigen 15-3), CEA (carcinoembryonic antigen), a contrast agent including a paramagnetic material such as iron oxide, manganese oxide, zinc oxide, gadolinium oxide, etc., and a therapeutic agent including an anticancer agent such as paclitaxel (PTX), doxorubicin (DOX), docetaxel (DOCE) and so on, an antibacterial agent, steroids, an anti-inflammatory painkiller, a sexual hormone, an immunosuppressive agent, an antiviral agent, an anesthetic, an antinauseant, an antihistamine agent, and a protein including bovine serum albumin, human serum albumin, human growth hormone, etc. In addition to the above components, additives typically known in the art, for example, excipients, stabilizers, pH-adjusting agents, antioxidants, preservatives, binders or disintegrants, etc., may be used.

The formation of the polymer micelles according to the present invention may include stirring, heating, ultrasound scanning, emulsification-assisted solvent evaporation, matrix formation or organic solvent-assisted dialysis, which may be used alone or in combinations thereof.

The diameter of the manufactured polymer micelles is not particularly limited, but may fall in the range of 10~200 nm. The polymer micelle-type pharmaceutical composition may be formulated into oral dosage forms or non-oral dosage forms, and may also be manufactured as an agent for vein, muscle or subcutaneous injection.

MODE FOR INVENTION

The following examples and test examples are set forth to illustrate but are not to be construed as limiting the present invention, in order to improve the understanding of the present invention.

Examples 1~10

Synthesis of pH-Sensitive Graft Copolymer

Examples 1

Production of poly(β-amino ester)polymer 1 mol of 3-amino-1-propanol and 1 mol of 1,4-butanediol diacrylate were placed in a two-neck round-bottom flask, and the mixture was allowed to react at 100° C. for 5 hours, thereby obtaining poly(β-amino ester) having a number average molecular weight (Mn) of 6,000.

Example 2

Production of poly(ethylene glycol)-poly(β-amino ester) graft polymer

To 1 mol of poly(β-amino ester) obtained in Example 1 were added 0.1 mol of poly(ethylene glycol) methyl ether (MPEG2000, Mn=2000) the terminal of which was substituted with a carboxyl group (with respect to the molecular weight of the monomer of poly(β-amino ester)), dicyclohexyl carboimide (DCC) and 4-(dimethyl amino)pyridine (DMAP), and the mixture was allowed to react at room temperature for 24 hours using dichloromethane as a solvent, after which a cyclo urea byproduct was separated, and the reaction product was precipitated in ethyl ether, yielding a poly(ethylene glycol)-poly(β-amino ester) graft polymer (Mn=12,600).

Example 3

A poly(ethylene glycol)-poly(β-amino ester) graft polymer having a Mn of 11,200 was obtained in the same manner as in Example 2, with the exception that 1.1 mol, not 1 mol, of 3-amino-1-propanol of Example 1 was used.

Example 4

A poly(ethylene glycol)-poly(β-amino ester) graft polymer having a Mn of 13,100 was obtained in the same manner as in Example 2, with the exception that 1 mol of 4-amino-1-butanol was used instead of 1 mol of 3-amino-1-propanol of Example 1.

Example 5

A poly(ethylene glycol)-poly(β-amino ester) graft polymer having a Mn of 14,500 was obtained in the same manner as in Example 2, with the exception that 1 mol of 5-amino-1-pentanol was used instead of 1 mol of 3-amino-1-propanol of Example 1.

Example 6

A poly(ethylene glycol)-poly(β-amino ester) graft polymer having a Mn of 14,000 was obtained in the same manner as in Example 2, with the exception that 1 mol of 6-amino-1-hexanol was used instead of 1 mol of 3-amino-1-propanol of Example 1.

Example 7

A poly(ethylene glycol)-poly(3-amino ester) graft polymer having a Mn of 14,100 was obtained in the same manner as in Example 2, with the exception that 0.3 mol, not 1 mol, of poly(β-amino ester) of Example 2 was used.

Example 8

A poly(ethylene glycol)-poly(β-amino ester) graft polymer having a Mn of 15,200 was obtained in the same manner as in Example 2, with the exception that 0.5 mol, not 1 mol, of poly(β-amino ester) of Example 2 was used.

Example 9

A poly(ethylene glycol)-poly(β-amino ester) graft polymer having a Mn of 19,200 was obtained in the same manner as in Example 2, with the exception that 1.5 mol, not 1 mol, of poly(β-amino ester) of Example 2 was used.

Example 10

To 1 mol of poly(ethylene glycol)-poly(β-amino ester) graft polymer obtained Example 2 were added 0.1 mol of deoxycholic acid (with respect to the molecular weight of the monomer of poly(ethylene glycol)-poly(β-amino ester)), DCC and DMAP, and the mixture was allowed to react at room temperature for 24 hours using tetrahydrofuran as a solvent, after which a dicyclo urea byproduct was separated, and the reaction product was precipitated in ethyl ether, yielding a poly(ethylene glycol)-poly(β-amino ester)-deoxycholic acid graft polymer (Mn=17,000).

Example 11

A poly(ethylene glycol)-poly(β-amino ester)-deoxycholic acid graft polymer (Mn=17,000) was obtained in the same manner as in Example 10, with the exception that 0.3 mol, not 0.1 mol, of deoxycholic acid of Example 10 was used.

Example 12

To 1 mol of poly(ethylene glycol)-poly(β-amino ester) graft polymer obtained in Example 2 were added 0.1 mol of cholesterol chloroformate (with respect to the molecular weight of the monomer of poly(ethylene glycol)-poly(β-amino ester)) and triethylamine, and the mixture was allowed to react at room temperature for 24 hours using tetrahydrofuran as a solvent, after which the reaction product was precipitated in ethyl ether, yielding a poly(ethylene glycol)-poly(β-amino ester)-cholesterol chloroformate graft polymer (Mn=17,000).

Example 13

To 1 mol of poly(ethylene glycol)-poly(β-amino ester)-cholesterol chloroformate graft polymer obtained in Example 12 were added 0.1 mol of biotin (with respect to the molecular weight of the monomer of poly(ethylene glycol)-poly(β-amino ester)-cholesterol graft copolymer), DCC and DMAP, and the mixture was allowed to react at room temperature for 24 hours using dichloromethane as a solvent, after which a dicyclo urea byproduct and unreacted biotin were separated, and the reaction product was precipitated in ethyl ether, yielding a biotin-poly(ethylene glycol)-poly(β-amino ester)-cholesterol graft polymer (Mn=17,500).

Test Example 1

Measurement of Molecular Weight of pH-Sensitive Graft Copolymer

In order to measure the molecular weight of the pH-sensitive graft copolymers manufactured according to the present invention, the following analysis was carried out.

Figure 3:
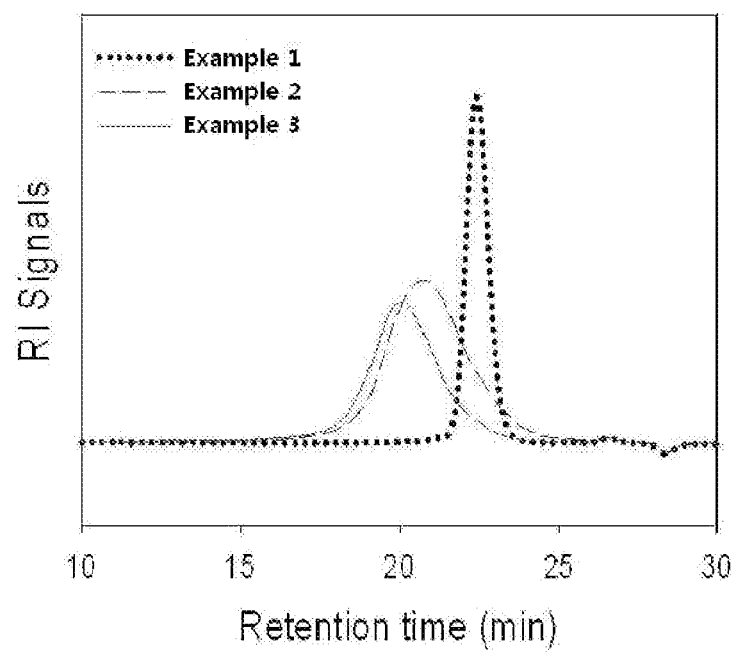
FIG. 3 is a GPC graph showing changes in refractive index of poly(β-amino ester) and a pH-sensitive graft copolymer obtained in Examples 1 and 2, with respect to time.
Figure 4:
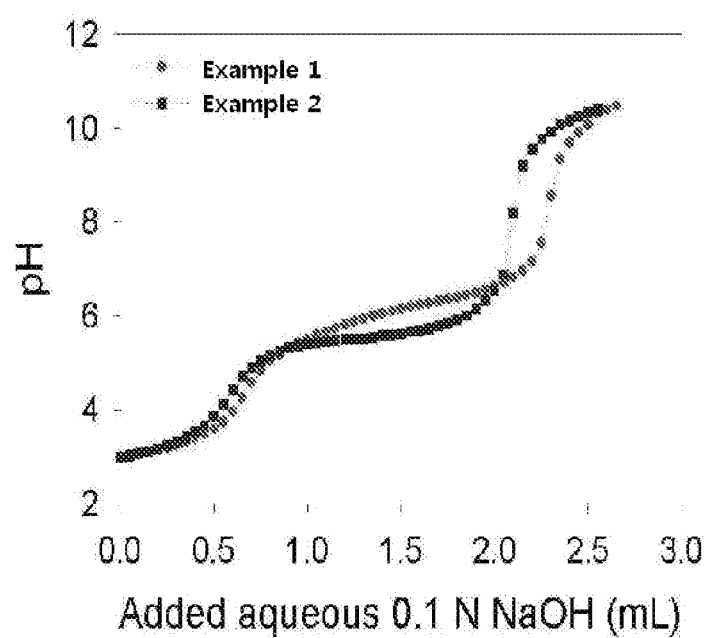
FIG. 4 is a graph showing the pKb of the pH-sensitive graft copolymer of Examples 1 and 2, determined via titration using a NaOH aqueous solution.

The poly(β-amino ester) and the graft copolymers including the same obtained in Examples 1 to 13 were used, and to examine whether the molecular weight thereof could be adjusted, gel permeation chromatography (GPC, available from Waters) analysis was performed. FIG. 3 shows the GPC diagrams of poly(ethylene glycol) the terminal of which was substituted with a carboxylic group, poly(β-amino ester) and the graft copolymer using the same, in that order, wherein the molecular weight could be calculated from the retention time.

Test Example 2

Measurement of Critical Micelle Concentration

In order to observe the behavior of the pH-sensitive graft copolymer micelles manufactured according to the present invention in relation to changes in pH, the following test was carried out.

Even when the critical micelle concentration (CMC) of the graft copolymers obtained in Examples 2, 10, 11 was measured using a fluorescence spectrometer, no changes in the behavior of the micelles were immediately apparent, and thus a hydrophobic light-emitting material, namely, pyrene was used.

Figure 5:
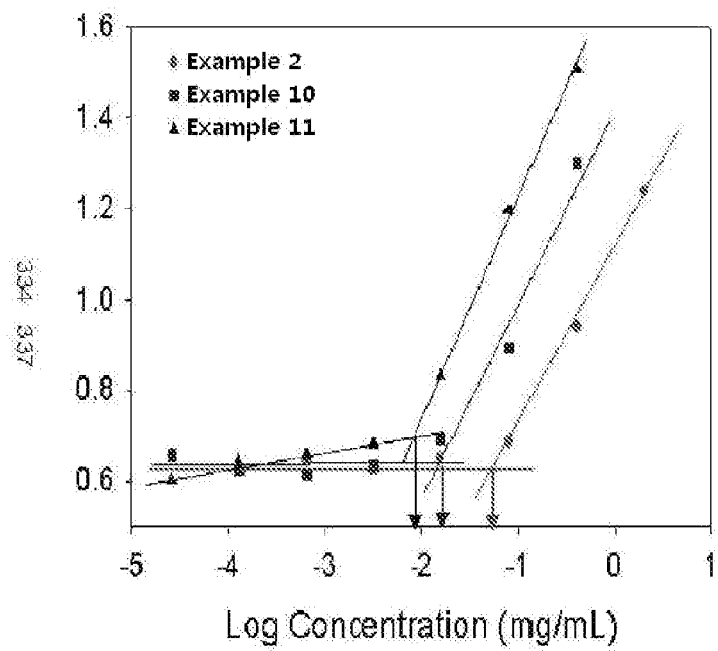
FIG. 5 is a graph showing the critical micelle concentration of pH-sensitive graft copolymers obtained in Examples 2, 10, 11, as measured using a fluorescence spectrometer.

A buffer solution, pH 7.0, containing $10^{-6}$ M pyrene was made, and the sample obtained in Examples 2, 10, 11 was dissolved in a concentration of 2 mg/Ml in the buffer solution, and then serially diluted by ⅕. Using a fluorescence spectrometer, changes in emitted energy resulting from changes in concentration of the micelles were measured. As shown in FIG. 5, as the amount of the hydrophobic deoxycholic acid grafted to the graft copolymer was increased, the CMC decreased.

Test Example 3

Measurement of pH Sensitivity of Graft Copolymer

Figure 6:
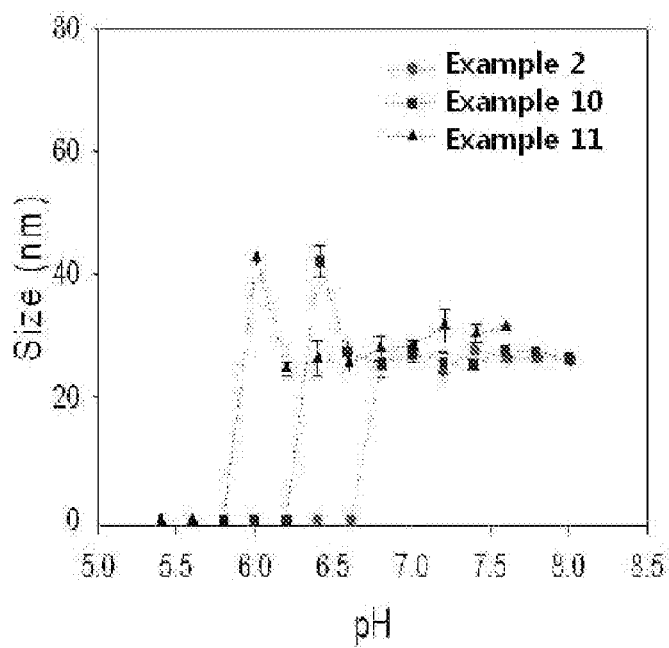
FIG. 6 is a graph showing micellization-demicellization transition and pH sensitivity of the pH-sensitive graft copolymers of Examples 2, 10, 11, in relation to changes in pH, as measured using DLS (Dynamic Light Scattering)

The pH sensitivity of the pH-sensitive graft copolymers manufactured according to the present invention was measured using DLS. As shown in FIG. 6, in the graft copolymers obtained in Examples 2, 10, 11, the micellization-demicellization transition in response to changes in pH was observed in the low pH range in proportion to the increase in amount of the grafted deoxycholic acid.

Test Example 4

Measurement of pH Sensitivity of Graft Copolymer

Figure 7:
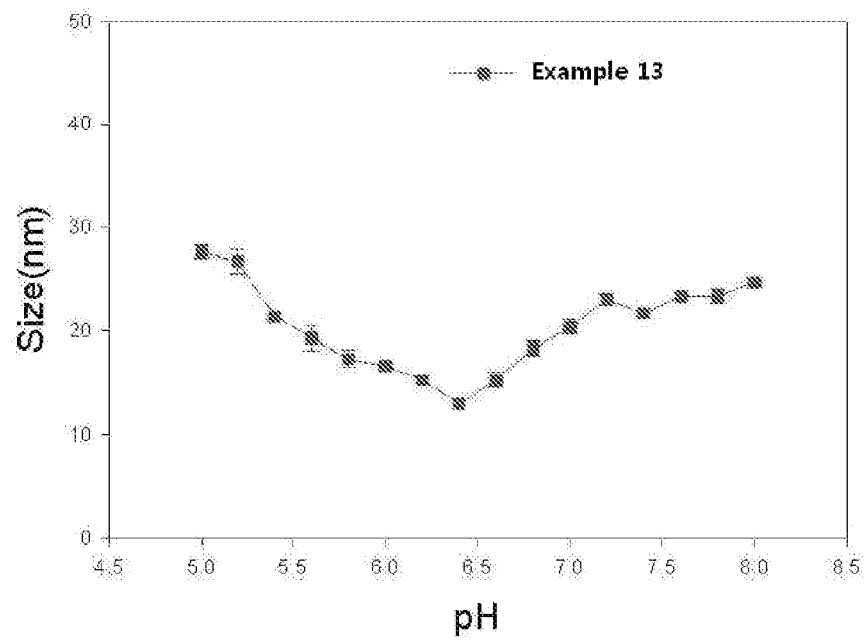
FIGS. 7 and 8 are graphs showing micellization-demicellization transition and pH sensitivity of a pH-sensitive graft copolymer obtained in Example 13, in relation to changes in pH, as measured using DLS.
Figure 8:
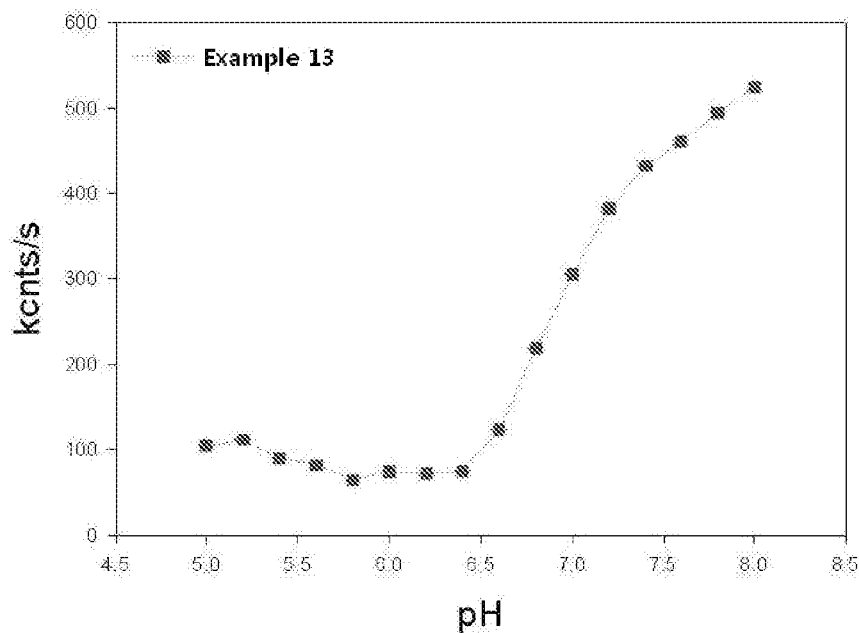

The pH sensitivity of the biotin-poly(ethylene glycol)-poly(β-amino ester)-cholesterol obtained in Example 13 was measured in the same manner as in Test Example 3. As shown in FIGS. 7 and 8, the micellization-demicellization transition of the graft copolymer in response to changes in pH was observed near pH 7.0.

Test Example 5

Measurement of the Degree of Action of Biotin in Relation to Changes in pH

Figure 9:
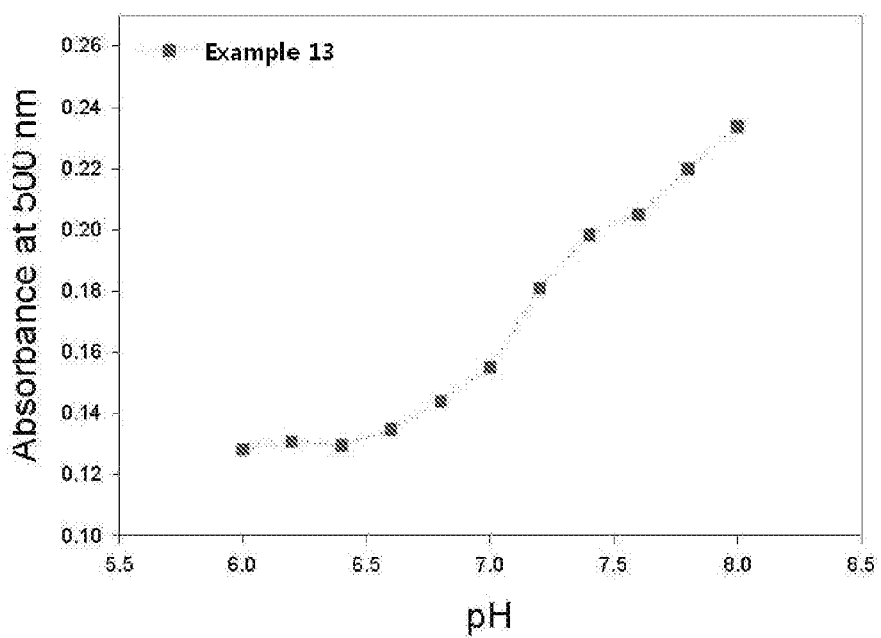
FIG. 9 is a graph showing the action of biotin of the pH-sensitive graft copolymer of Example 13, in relation to changes in pH, as measured via HABA-avidin assay.

The degree of action of the grafted biotin in the biotin-poly(ethylene glycol)-poly(β-amino ester)-cholesterol obtained in Example 13 in relation to changes in pH was measured via HABA-avidin assay. When HABA was physically bound to avidin, high absorbance was measured at 500 nm using a UV-vis spectrometer. However, when biotin approached the HABA-avidin bond, HABA was separated from avidin and the biotin was bound to avidin, thus decreasing the absorbance. Using this phenomenon, the effect relative to changes in the pH was analyzed. FIG. 9 shows changes in absorbance in relation to changes in pH, wherein the absorbance was lower at pH 6.5 than at pH 7.4. Because biotin does not come out of the surface of the micelles at pH 7.4, it has no influence on the HABA-avidin bond, but at pH 6.5, biotin comes out of the surface of the micelles, thereby allowing HABA to be separated from avidin. These results are based on the ionization of poly(3-amino ester), and thus biotin acts only on the cancer tissue, in lieu of acting on normal hematoceles or normal tissue, whereby the ability to target cancer cells is expected to be increased.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method of manufacturing a pH-sensitive graft copolymer as shown in the scheme below:

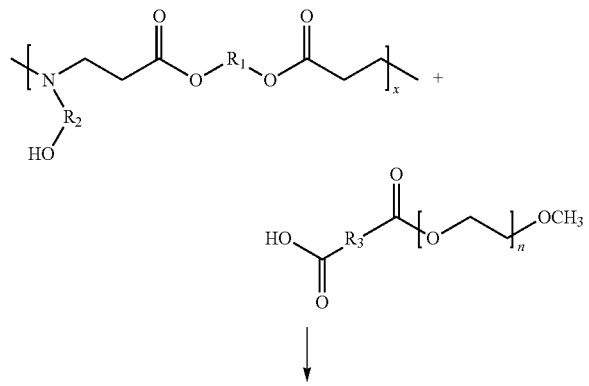

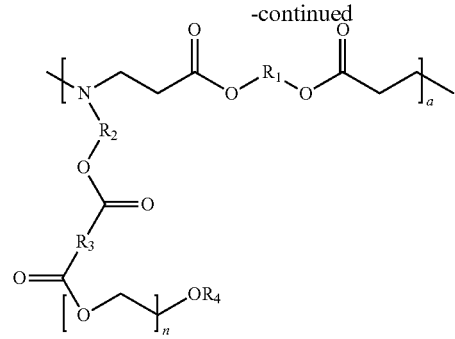

wherein $R_1$, $R_2$, $R_3$, and $R_4$ are a hydrogen atom or a C1-12 alkyl group; and a, b, x and n are a natural number ranging from 1 to 200.

2. The method of claim 1, wherein the graft copolymer is further derivatized as shown below:

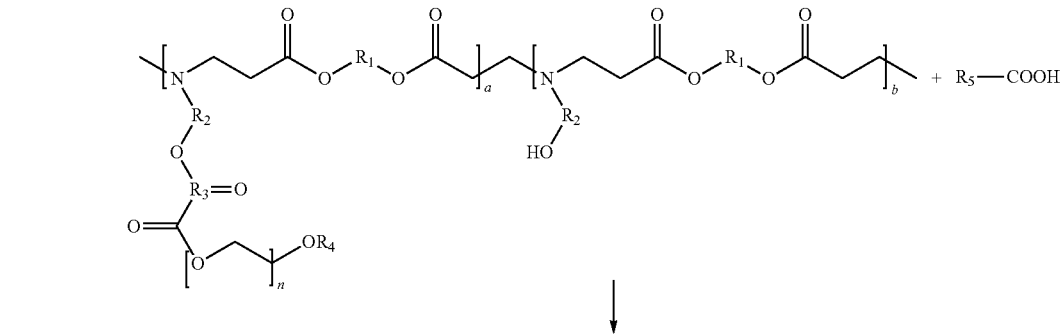

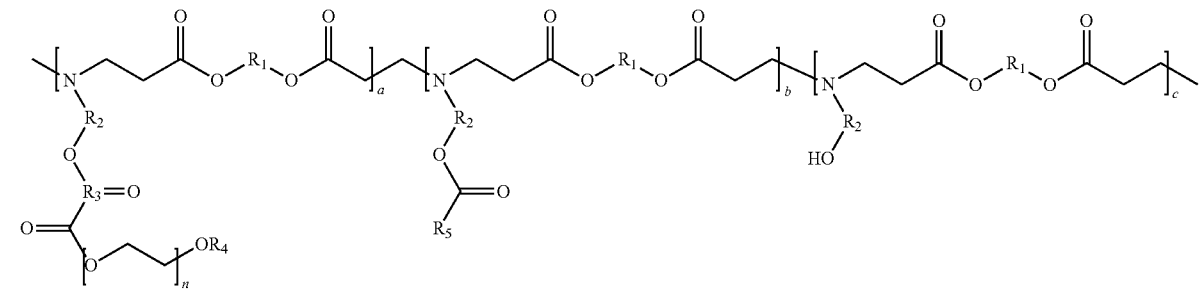

wherein $R_1$, $R_2$, $R_3$, and $R_4$ are a hydrogen atom or a C1-C12 alkyl group; a, b, c, d and n are a natural number ranging from 1 to 200; and $R_5$ is a bile acid based compound, a cholesterol based compound or a cancer-targeting factor.

3. The method of claim 1, wherein the graft copolymer is further derivatized as shown below:

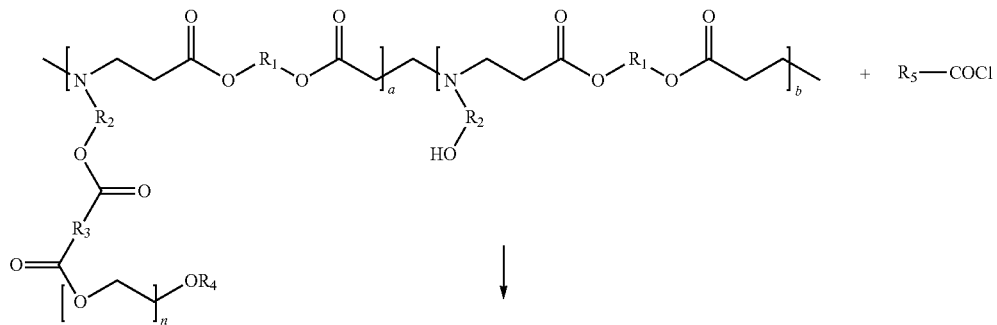

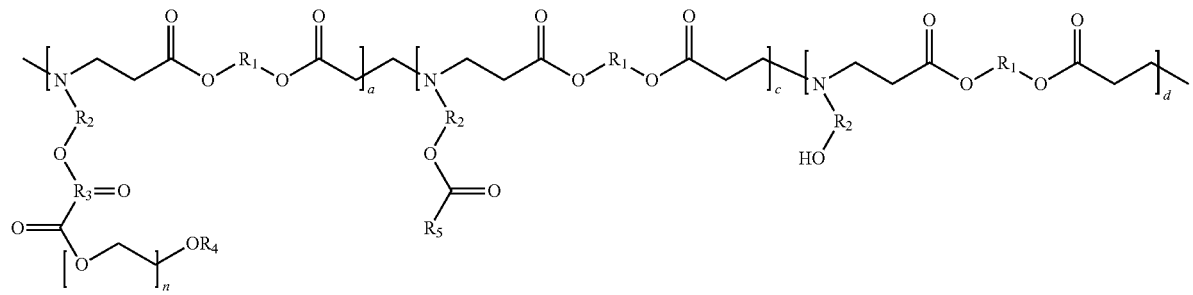

wherein $R_1$, $R_2$ and $R_3$, are a C1-C12 alkyl group; $R_4$ is a hydrogen atom or a C1-C12 alkyl group; a, b, c, d and n are a natural number ranging from 1 to 200; and $R_5$ is a cholesterol based compound.

4. The method of claim 1, wherein the graft copolymer is further derivatized as shown below:

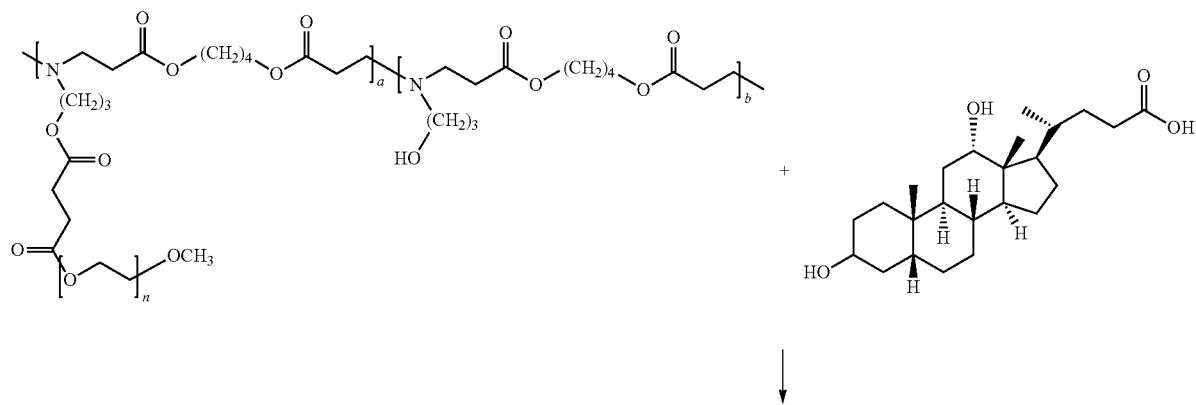

-continued
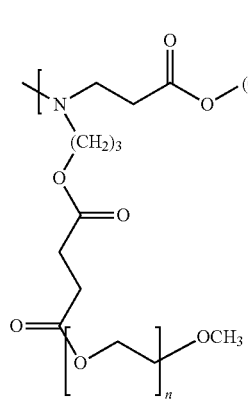
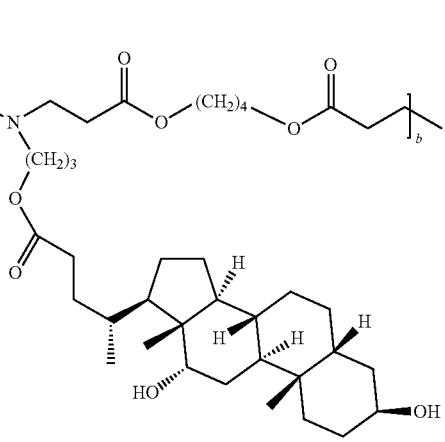
wherein a, b, c, d and n are a natural number ranging from 1 to 200.
5. The method of claim 1, wherein the graft copolymer is further derivatized as shown below:
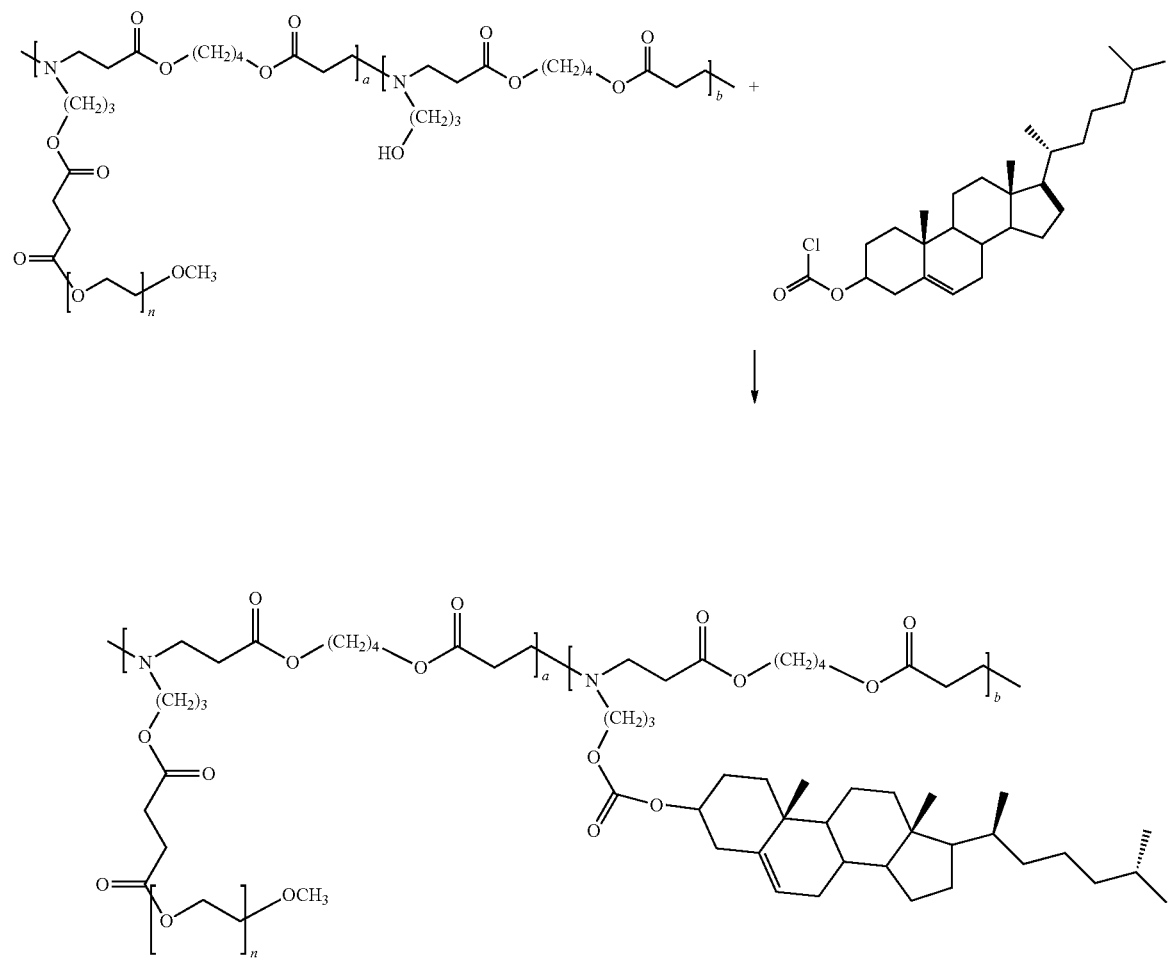
wherein a, b, c, d and n are a natural number ranging from 1 to 200.
6. The method of claim 5, wherein the pH-sensitive graft copolymer is further derivatized as shown below:

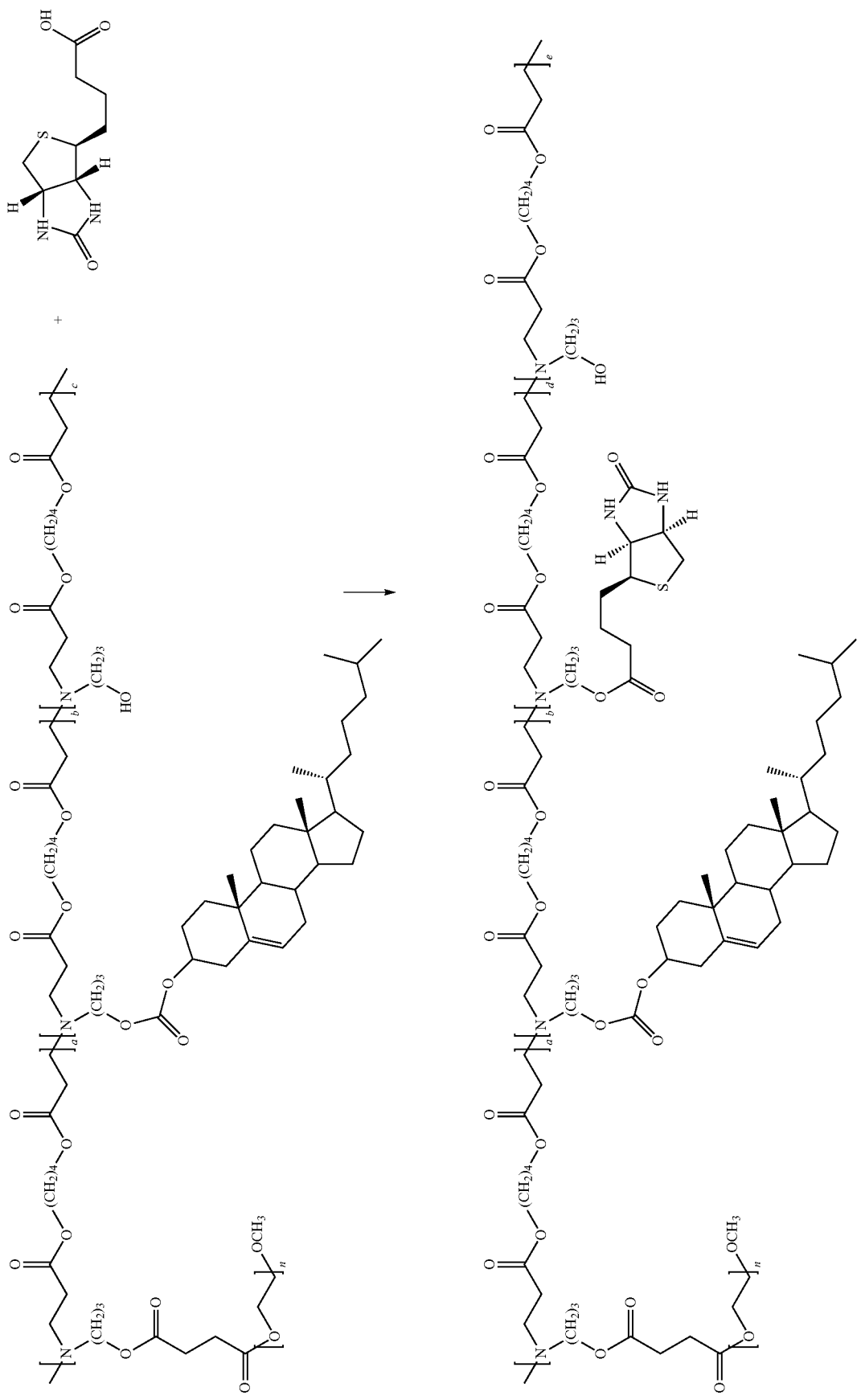

wherein a, c, d, e, f and n are a natural number ranging from 1 to 200.

* * * * *